(12) United States Patent
Veiseh et al.

(10) Patent No.: US 9,952,122 B2
(45) Date of Patent: Apr. 24, 2018

(54) POLYSENSING BIOELECTRONIC TEST PLATE

(71) Applicant: Palo Alto Research Center Incorporated, Palo Alto, CA (US)

(72) Inventors: Mandana Veiseh, Menlo Park, CA (US); JengPing Lu, Fremont, CA (US); Eugene M. Chow, Fremont, CA (US); David K. Biegelsen, Portola Valley, CA (US); Ramkumar Abhishek, Menlo Park, CA (US); Felicia Linn, San Jose, CA (US)

(73) Assignee: Palo Alto Research Center Incorporated, Palo Alto, CA (US)

(*) Notice: Subject to any disclaimer, the term of this patent is extended or adjusted under 35 U.S.C. 154(b) by 294 days.

(21) Appl. No.: 14/816,849

(22) Filed: Aug. 3, 2015

(65) Prior Publication Data
US 2017/0038282 A1 Feb. 9, 2017

(51) Int. Cl.
G01N 29/02 (2006.01)
G01N 21/25 (2006.01)
G01N 1/10 (2006.01)

(52) U.S. Cl.
CPC .......... G01N 1/10 (2013.01); G01N 21/253 (2013.01); G01N 29/02 (2013.01)

(58) Field of Classification Search
CPC ......... G01N 1/10; G01N 29/02; G01N 21/253
USPC .......................................................... 73/649
See application file for complete search history.

(56) References Cited

U.S. PATENT DOCUMENTS

| | | | |
|---|---|---|---|
| 7,405,582 B2 * | 7/2008 | Mineo | G01R 1/0408 324/754.08 |
| 7,470,544 B2 | 12/2008 | Sharma | |
| 8,283,936 B2 | 10/2012 | Iqbal et al. | |
| 8,835,247 B2 | 9/2014 | De Langen et al. | |
| 2003/0150257 A1 * | 8/2003 | Mutz | B01L 3/0268 73/61.49 |
| 2004/0040868 A1 | 3/2004 | DeNuzzio et al. | |
| 2005/0054028 A1 | 3/2005 | Teich et al. | |

(Continued)

FOREIGN PATENT DOCUMENTS

EP 2295988 3/2011

OTHER PUBLICATIONS

Office action dated Nov. 16, 2016 from EP App. No. 16181504.8, 10 pages.

(Continued)

*Primary Examiner* — J M Saint Surin
(74) *Attorney, Agent, or Firm* — Hollingsworth Davis, LLC

(57) ABSTRACT

An electronic test plate includes a test plate comprising plurality of wells, each well configured to contain a substance to be analyzed. Sensors are arranged to sense characteristics of the substance and to generate sensor signals based on the sensed characteristics over time. The sensors are arranged so that multiple sensors are associated with each well. At least one sensor of the multiple sensors senses a characteristic of the substance that is different from a characteristic sensed by another sensor of the multiple sensors. Sensor select circuitry is arranged on a backplane disposed along the test plate. The sensor select circuitry is coupled to the sensors and enable the sensor signals of selected sensors to be accessed at a data output of the backplane.

29 Claims, 19 Drawing Sheets

(56) References Cited

U.S. PATENT DOCUMENTS

| | | |
|---|---|---|
| 2005/0176155 A1 | 8/2005 | Klein et al. |
| 2005/0212869 A1* | 9/2005 | Ellson .................. B01L 3/0268 347/75 |
| 2006/0071983 A1* | 4/2006 | Stearns ................ B41J 2/14008 347/68 |
| 2008/0014571 A1 | 1/2008 | Teich et al. |
| 2014/0273191 A1 | 9/2014 | Tipgunlakant et al. |
| 2014/0274760 A1 | 9/2014 | Fomina et al. |

OTHER PUBLICATIONS

Veiseh et al. "Guided cell patterning on gold-silicon dioxide substrates by surface molecular engineering," Biomaterials 25 (2004) 3315-3324.

Veiseh et al. "Effect of silicon oxidation on long-term cell selectivity of cell-patterned Au/SiO2 platforms", J. Am. Chem. Soc. 128 (2006), 1197-1203.

Veiseh et al. "Single-cell-based sensors and synchrotron FTIR spectroscopy: A hybrid system towards bacterial detection" Biosensors and Bioelectronics 23 (2007) 253-260.

Niazi et al., "Development of Oxygen Sensor by Integrating the Low Cost Printed Circuit Board Technology and Solid Electrolyte Membrane", Proceedings of the International Conference on Biomedical Engineering and Systems, Paper N. 137, Aug. 14-15, 2014, 7 pages.

Toon, "End of Microplates? Novel Electronic Biosensing Technology Could Facilitate a New Era of Personalized Medicine", Georgia Tech Research News, Sep. 19, 2010, 4 pages.

Yen et al., "Improvement in pH Sensitivity of Low-Temperature Polycrystalline-Silicon Thin-Film Transistor Sensors Using H2 Sintering", Sensors, 2014, 3825-3832.

Eversmann et al., "A 128×128 CMOS Biosensor Array for Extracellular Recording of Neural Activity", IEEE Journal of Solid-State Circuits, vol. 38, No. 32, Dec. 2003, pp. 2306-2317.

* cited by examiner

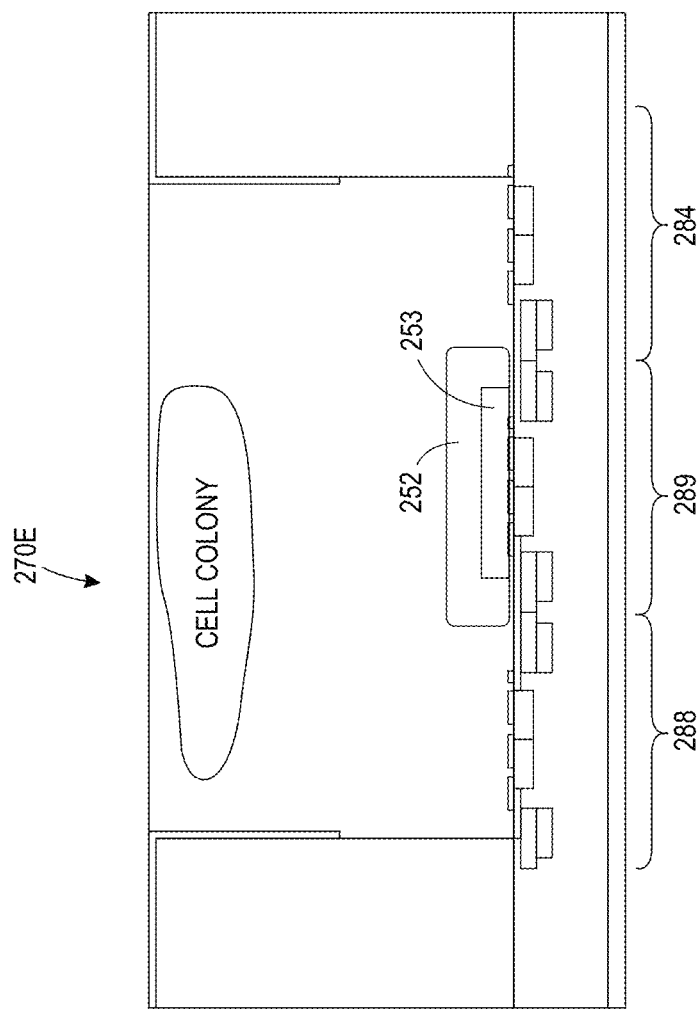

POLYSENSING BIOELECTRONIC TEST PLATE

TECHNICAL FIELD

This disclosure relates generally to test plates for analyzing substances and to systems and methods related to such test plates.

BACKGROUND

A number of applications in biology, medicine, and toxicology involve real-time sensing of complex biophysical, biochemical, and functional characteristics of cells in physiologically-relevant 3D environments. Because these characteristics may alter heterogeneously and transiently during progression from normal to disease state and/or upon exposure to drugs and toxicants, it is desirable for cells (in single or colony states) to be monitored in parallel and continuously.

SUMMARY

Some embodiments are directed to an electronic test plate that includes a test plate comprising plurality of wells, each well configured to contain a substance to be analyzed. Sensors are configured to sense characteristics of the substance and to generate sensor signals based on the sensed characteristics. The sensors are arranged so that multiple sensors are associated with each well. At least one sensor of the multiple sensors senses a characteristic of the substance that is different from a characteristic sensed by another sensor of the multiple sensors. Sensor select circuitry is coupled to the sensors. The sensor select circuitry is arranged on a backplane disposed along the test plate. The sensor select circuitry enables the sensor signals of selected sensors to be accessed at a data output of the backplane. According to some aspects, the electronic test plate is optically transparent or includes optically transparent regions that allow the wells to be optically interrogated.

According to some embodiments, an electronic test plate includes a test plate comprising plurality of wells, each well configured to contain a substance to be analyzed. Sensors of the electronic test plate are configured to sense characteristics of the substance and to generate sensor signals based on the sensed characteristics. The sensors are arranged so that multiple sensors are associated with each well. At least one sensor of the multiple sensors is configured to sense a characteristic of the substance that is different from a characteristic sensed by another sensor of the multiple sensors. Sensor select circuitry of the electronic test plate arranged on a backplane that extends along the test plate is coupled to the sensors. The sensor select circuitry enables the sensor signals of selected sensors to be accessed at a data output of the backplane. Readout circuitry receives and processes the selected sensor signals present at the data output.

Some embodiments are directed to a method of making an electronic test plate. The method includes forming a test plate comprising a plurality of wells, each well configured to contain a substance to be analyzed. Electronic circuitry including multiple sensors and sensor select circuitry coupled to the sensors is fabricated. The multiple sensors are configured to sense characteristics of the substance and to generate sensor signals based on the sensed characteristics. The sensor select circuitry enables the sensor signals of selected sensors to be accessed at a data output of the backplane. The sensors are arranged with respect to the wells so that multiple sensors are associated with each well. Each of the multiple sensors associated with a well are configured to sense a characteristic of the substance that is different from characteristics sensed by another sensor of the multiple sensors.

Some embodiments involve a method that includes sensing multiple characteristics of a substance to be analyzed disposed in wells of a test plate. The multiple characteristics are sensed using multiple sensors associated with each well. At least one of the multiple sensors is configured to sense a characteristic of the substance that is different from a characteristic sensed by another of the multiple sensors. Sensor signals are generated based on the sensed characteristics over time. Address lines are activated to enable sensor signals of selected sensors to be accessed at a data output.

BRIEF DESCRIPTION OF THE DRAWINGS

The discussion below makes reference to the following figures, wherein the same reference number may be used to identify the similar/same component in multiple figures. Unless otherwise indicated, the figures are not necessarily made to scale.

FIG. 2E is a cross sectional diagram showing a pixel that includes an oxygen sensor in accordance with some embodiments;

DETAILED DESCRIPTION

Figure 1A:
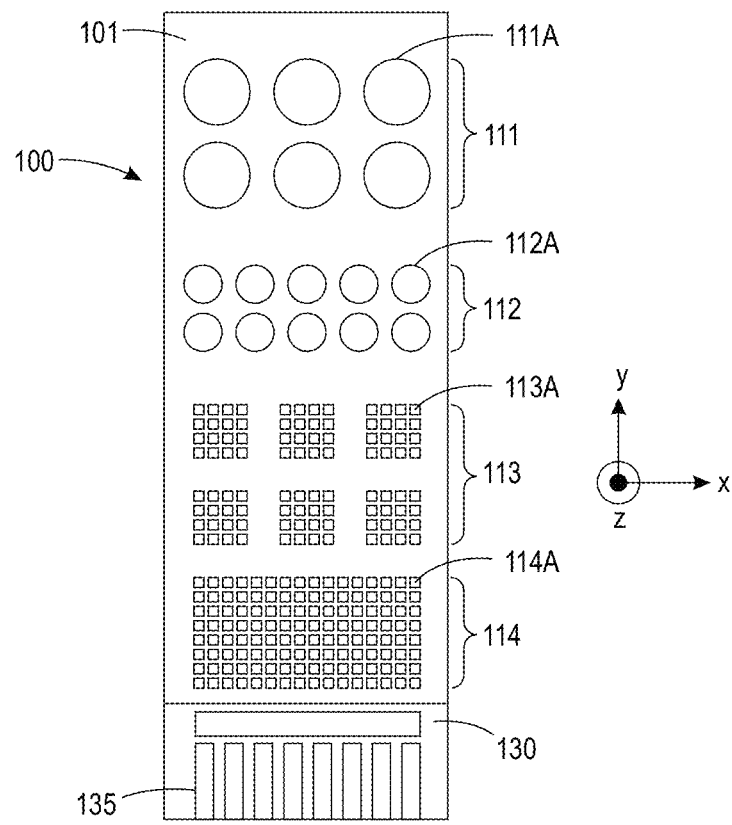
FIG. 1A is a top view of an electronic test plate in accordance with some embodiments.

Embodiments disclosed herein involve a polysensing electronic test plate comprising a test plate having plurality of test wells and multiple sensors associated with each test well. The multiple sensors sense characteristics of a substance to be analyzed disposed in the test wells and generate sensor signals based on the sensed characteristics. At least one of the multiple sensors associated with a test well can sense a characteristic of the substance that is different from a characteristic sensed by another of the multiple sensors. In some embodiments, one or more of the sensor may be configured to sense a characteristic of the substance in multiple dimensions, e.g., 2D or 3D sensing. Sensor select circuitry enables access to the sensor signals of selected sensors at a data output of the electronic test plate. In some embodiments, the sensor select circuitry can comprise thin film transistor (TFT) switches disposed on a backplane that are activated by select lines to access the sensor outputs.

In some implementations, each test well has at least one optically transparent bounding region allowing the electronic test plate disclosed herein to be useable in conjunction with various types of optical-based analytical techniques that interrogate live or fixed cells and tissues, such as optical microscopy, spectral analysis, analysis by fluorescence tagging, in addition to other types of analysis such as mass spectrometry, atomic force microscopy, Fourier transform infrared spectromicroscopy, Raman spectroscopy, and scanning electron microscopy. Optical-based analytical techniques can include both label-free and label-specific techniques. In some embodiments, these analytical techniques can be used to supplement and/or confirm results achieved using the multiple sensors of the electronic test plate. The electronic test plate described in embodiments herein can be suitable for use with various analytical techniques in addition to polysensing by the multiple sensors. Additional analytical techniques that may be useful in conjunction with the disclosed polysensing electronic test plate are discussed in Veiseh, Mandana, et al. "Guided cell patterning on gold-silicon dioxide substrates by surface molecular engineering," Biomaterials 25 (2004) 3315-3324, Veiseh, Mandana, et al. "Effect of silicon oxidation on long-term cell selectivity of cell-patterned Au/SiO2 platforms", J. AM. CHEM. SOC. 128 (2006), 1197-1203, and Veiseh, Mandana, et al. "Single-cell-based sensors and synchrotron FTIR spectroscopy: A hybrid system towards bacterial detection" Biosensors and Bioelectronics 23 (2007) 253-260, which are incorporated by reference herein.

The embodiments disclosed herein can also be used to fill a major gap in physiologically relevant cell-based sensing for applications in biology, medicine, and environmental toxicology. These approaches provide a new tool for biological and clinical evaluations of heterogeneity in environments that reproduce aspects of an in vivo microenvironment, personalized medicine, and analyte screening in both healthcare and toxicology fields. They may also reveal new multiplexed biomarkers and temporal/spatial correlations that would otherwise be missed by static and label-specific measurements on fixed cells or summing of single mode biomarkers sensed by separate equipment or at different times. Orders of magnitude more data can be collected than from existing approaches, as different biomarkers can be monitored simultaneously and continuously, and multiplexed on massively parallel cell sensor arrays. This increases the potential for identifying low incidence heterogeneities, new transient signals, or phenotypic patterns via machine learning algorithms. Comparison of neighboring wells that differ in only one respect can provide differential information allowing high levels of common mode noise rejection.

Figure 1B:
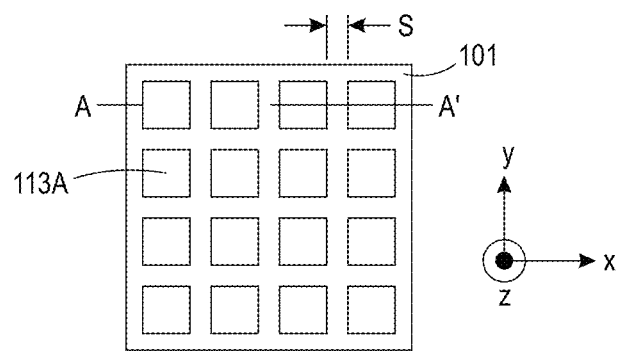
FIG. 1B shows a top view of a section of the test plate of FIG. 1.
Figure 1C:
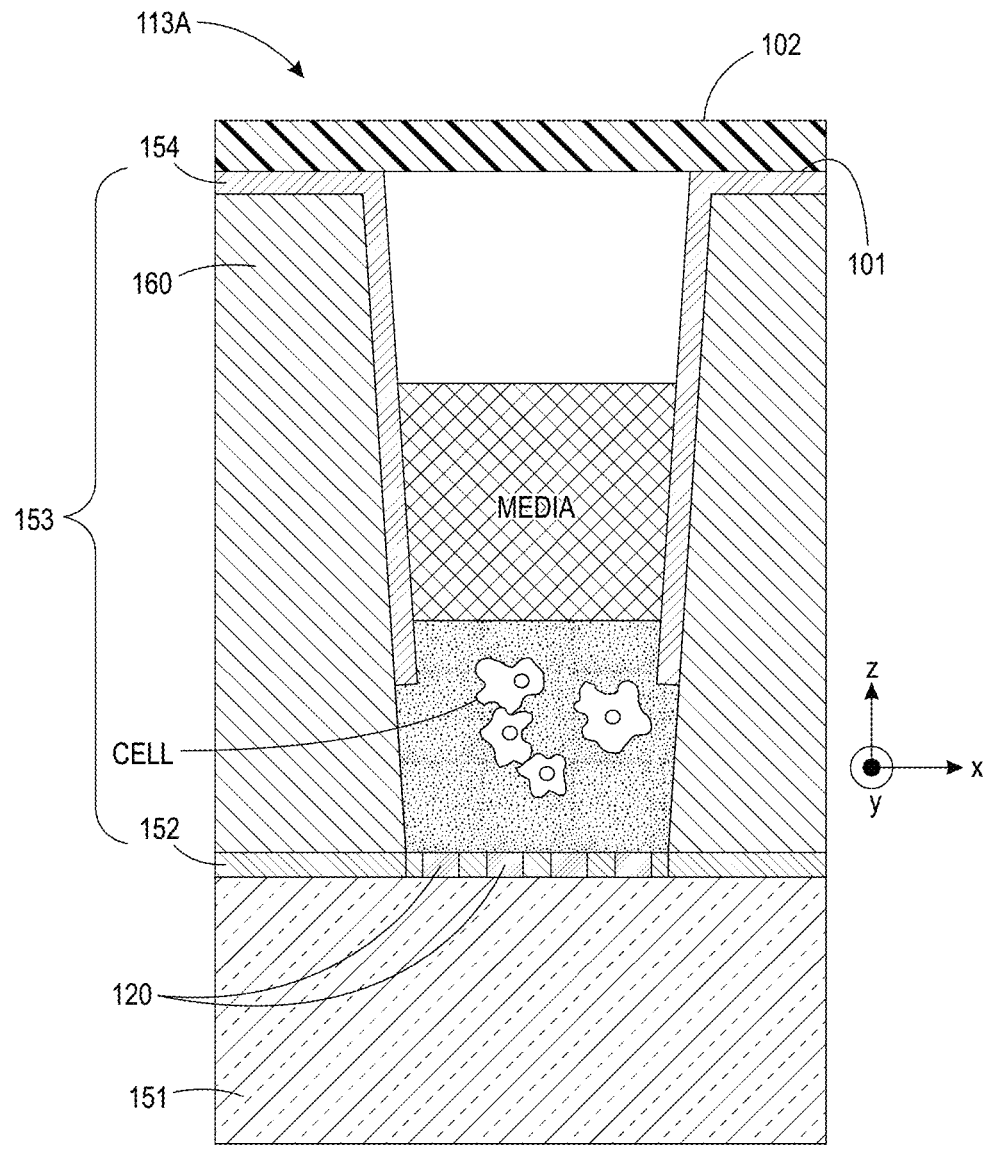
FIG. 1C shows a cross sectional view of a test well and multiple sensors associated with the test well.
Figure 1D:
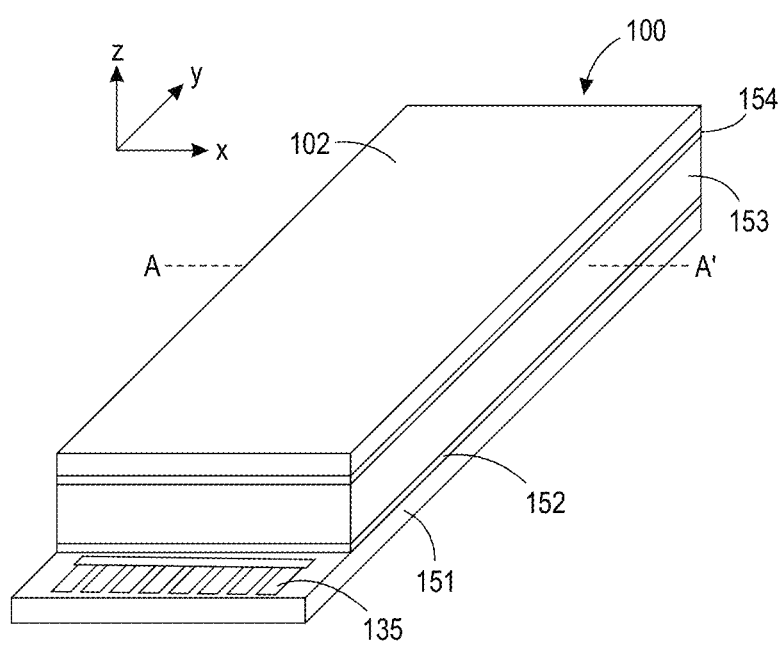
FIG. 1D is a simplified perspective view of the layers of a portion of the electronic test plate of FIG. 1A.

FIG. 1A is a top view of an electronic test plate 100 in accordance with some embodiments; FIG. 1B shows a top view of a section of the test plate 100; FIG. 1C shows a cross sectional view of a test well and multiple sensors associated with the test well taken along plane A-A'; FIG. 1D is a perspective view of a portion of the electronic test plate.

The electronic test plate 100 includes a plurality of test wells 111a-114a defined by well walls 160 that extend in the z direction below the top surface 101 of the test plate 100. The test wells 111a-114a shown in FIG. 1A may be arranged in a variety of patterns and/or sizes, e.g., diameters and/or depths, as illustrated in FIG. 1A. As shown, the test plate 100 includes four sections 111-114, each section having test wells 111a-114a wherein the diameters of the test wells 111a-114a are different from section-to-section. In one particular example, the diameter of the test wells 111a in section 111 of the test plate 100 have a diameter of 5 mm at the surface 101 of the test plate 100; the diameter of the test wells 112a in section 112 of the test plate 100 have a diameter of 3.1 mm at the surface 101 of the test plate 100; the diameter of the test wells 113a in section 113 of the test plate 100 have a diameter of 1 mm at the surface 101 of the test plate 100; and the diameter of the test wells 114a in section 114 of the test plate 100 have a diameter of 1 mm at the surface 101 of the test plate 100. Test wells 114a are arranged in a pattern that is denser (more test wells per area) than the pattern of section 113. It will be appreciated that the forgoing example is just one of many configurations for test wells in a test plate. Furthermore, although test plates that include different sizes and patterns of test wells (e.g. rectangular or triangular) are possible, in many applications the test plate comprises test wells that are equally spaced and/or each test well is the same size, having the same diameter.

Multiple sensors 120 are associated with each test well 111a-114a. The multiple sensors 120 associated with a test well 111a-114a sense multiple characteristics of the substance in the test well. Each of the sensors is configured to sense a characteristic of the substance in one, two, or three dimensions. For example, one or more of the sensors 120 may be configured to sense a characteristic of the substance across at least a portion of the test well along the x direction; the one or more sensors may additionally be configured to sense the characteristic across at least a portion of the test well along the y direction; and the one or more sensors may additionally be configured to sense the characteristic across at least a portion of the test well along the z direction, thus providing one, two, or three dimensional sensing over time.

The sensors 120 associated with each test well 111a-114a may be arranged in clusters of multiple sensors of different types wherein each cluster of sensors is referred to herein as a "pixel." Each sensor in a pixel is referred to herein as a "subpixel." Each sensing subpixel of a pixel can be configured to measure a characteristic that is different from a characteristic of the substance sensed by another sensing subpixel of the pixel. It will be appreciated that the terminology, "pixel" and "subpixel" is borrowed from display or imaging devices, wherein "pixel" describes the unit cell of combination of sensing detection units ("subpixels") that can be repeated into a 2D array.

The sensor pixels and subpixels may have the same spacing pitch on the backplane regardless of whether the test plate includes large, e.g., 5 mm diameter, test wells, or small, e.g., 1 mm test wells. More pixels can be associated with each larger test well when compared to the number of pixels associated with smaller test wells. In some embodiments, the pixel pitch may be on the order of about 300 µm, for example. It is possible for the pixel pitch to be less than 300 µm, e.g., about 90 or even about 60 µm in some implementations.

The number of pixels per test well and/or the number of subpixels per pixel achievable depends on the size of the test wells and/or the dimensions of the plate. FIG. 1A illustrates a test plate having a width of 25 mm along the x axis and a length of 75 mm, along the y axis, although other dimensions are possible, such as a standard culture plate, e.g., 127.7 mm×85.5 mm. In a first example configuration, a 25 mm×75 mm test plate may have 15 equally spaced test wells having a circular x-y cross section (as illustrated by section 111 of test plate 100) with a diameter of 5 mm and 218 pixels associated with each test well. In a second example, a 25 mm×75 mm test plate may have 50 equally spaced circular test wells (as illustrated by section 112 of test plate 100), each test well having with a diameter of 3.1 mm and 80 pixels associated with each test well. In a third example, a 25 mm×75 mm test plate may have 288 square test wells (arranged in a pattern illustrated by section 113 of test plate 100) each test well having with length along the y axis of 1 mm and width along the x axis of 1 mm and 10 pixels associated with each test well. In a fourth example, a 25 mm×75 mm test plate may have 592 equally spaced square test wells (as illustrated by section 114 of test plate 100) each test well having with a length and width of 1 mm and 10 pixels associated with each test well. In the first example, assuming each pixel includes four sensing subpixels per pixel, the backplane includes 3,270 pixels and 13,080 sensors; in the second example, the backplane includes 4,000 pixels and 16,000 sensors; in the third example, the backplane includes 2,880 pixels and 11,520 sensors; and in the fourth example, the backplane includes 5,920 pixels and 23,680 sensors. These values are merely examples and a backplane may include more or fewer pixels and subpixels. In some embodiments, test plate can be configured to provide about 40,000 sensors providing 40,000 unique measurements.

In some applications, the distance, S, between wells may be about 5% of the diameter (or length or width) of the test wells. For example, for equally spaced square test wells having a width and length of 1 mm, the test walls may be spaced apart along the x axis by 20% of the width of the test wells (0.2 mm) and may be spaced apart along the y axis by 20% of the length of the test wells (0.2 mm).

The electronic test well may be smaller or larger than the 25 mm×75 mm test plate illustrated in FIG. 1. According to some embodiments described herein, the electronic test well comprises integrated thin film transistor (TFT) based electronics and active matrix electronics addressing, enabling connections to a very large number of sensors over low cost, large area glass slides for cell culture well plate arrays. The integrated multiplexed array enables many unique measurements per slide (e.g., 4 measurements per pixel) with only a few addressing pads and, depending on the application, is readily expandable to a variety of sizes.

These examples are provided for the purposes of illustration and the reader will understand that test plates of other dimensions, test wells having other patterns, cross sectional shapes (e.g., rectangular, triangular), sizes, and spacings, and other numbers of sensors associated with each test well are possible and fall within the scope of this disclosure.

As best seen in FIG. 1C, in some embodiments, the electronic test plate 100 may include a cap layer 102 to retain the substance within the wells and to reduce or prevent contamination of the substance. In some configurations, the cap layer comprises a patterned layer of individual caps disposed over the test wells. In other configurations, the cap layer is a continuous layer that spans over the top surface of the test plate. The cap layer can comprise a transparent material, e.g., a transparent plastic such as polycarbonate or polystyrene.

The electronic test plate 100 illustrated in FIGS. 1A through 1D is a structure comprising a number of material layers. The electronic test plate 100 includes a substrate 151 that provides mechanical support for additional layers which are disposed thereon. In some implementations, the substrate 151 may comprise glass or other optically transparent material having a thickness along the z direction of 800 µm. Other thicknesses and/or materials could be used for the substrate as long as they allow sufficient mechanical rigidity to facilitate handling of the electronic test plate 100 and/or optical transparency to facilitate use of the electronic test plate with optical analytical techniques.

The electronic test plate, cap layer and any portion of the test plate that interface with substance may be sterile or serializable with common techniques such as radiations, gas, chemical, or heat sterilization.

The backplane 152 is disposed on the substrate 151 and may include multiple sublayers that form electronic devices with electrical connections therebetween. In some embodiments, the backplane may have a thickness along the z direction on the order of about 5 µm. The backplane 152 includes sensors 120 associated with the test wells 111a-114a and circuitry 130 such as switches that provide access to the sensors. In some embodiments, the backplane 152 may also include additional electronic circuitry such as signal processing circuitry, control circuitry, memory circuitry and/or communications circuitry, e.g., wired or wireless communications circuitry as discussed in more detail herein. The backplane 152 also includes electrical contacts 135, e.g., arranged as an edge card connector, used to communicatively couple the sensors and/or other circuitry of the electronic test plate 100 to another device such as a host processor 100 in accordance with some embodiments.

The device includes optically transparent regions that allow each well to be optically interrogated. The electronic devices on the backplane 152 may comprise thin film electronic devices, e.g., thin film transistors (TFTs) comprising optically transparent semiconductors and/or optically thin metal or optically transparent electrical conductors such as indium tin oxide (ITO), so as to allow light to pass through the backplane and into the wells. To facilitate the use of the electronic test plate with various optical analysis techniques, e.g., optical microcopy, etc., the backplane is optically transparent at least at the interfaces between each test well and the backplane. In some embodiments, the entire backplane is optically transparent. In some embodiments, portions of the backplane, e.g., regions between the test wells are optically opaque. In some embodiments, the entire backplane may be optically opaque. In various configurations, the electronic test plate can be optically interrogated from either or both of the top and the bottom of the wells A test plate layer 153, e.g., having a thickness in the z direction on the order of about 1500 μm is disposed on the backplane 152. In some embodiments, the material of the test plate layer 153 may comprise a plastic or other material that can be patterned to form the test wells 111a-114a. The test wells 111a-114a are defined by well walls 160 that extend between a top electrical contact layer 154 and the backplane 152. The top electrical contact layer 154 is an electrically conductive layer and may comprise a metal (such as gold), a metal alloy, or other electrically conductive material. The top electrical contact layer 154 is disposed over the test plate layer 153 and conformally coats at least a portion of the test well walls. The test plate layer 153 may have a thickness along the z direction on the order of about 1500 μm. The top electrical contact layer may be a thin metal such as gold, or other conductive material. For example, the thickness of the top electrical contact along the z axis may be in a range of about 0.1 to about 1 μm.

In some embodiments, the test plate layer 153 is formed directly on the backplane 152—this structure is referred to herein as a unitary electronic test plate. In other embodiments, the well layer 153 and the backplane are each separately fabricated and the well layer 153 is bonded to the backplane 152. The test wells may contain a hydrogel, e.g. a 3D laminin rich gel such as MATRIGEL available from Corning, Inc., located in Corning N.Y., or CULTREX BME available from Trevigen, Inc., located in Gaithersburg, Md. to facilitate 3D growth of cells cultured within the test wells. The substance to be analyzed may include live cells, bacteria, viruses, fungus, microbes, cell compartments, exosomes, molecules, macromolecules, enzymes or tissue components grown in a three dimensional environment.

The substance to be analyzed may comprise live cells and/or tissue components, for example, that grow in the hydrogel. Tissue components may be composed of different cell types, extracellular materials including proteins, sugars, fat, carbohydrates etc. For instance a cancer tissue is composed of cancer cells, immune cells, nerve cells, fibroblasts, etc. and many acellular components. In some embodiments, the substance to be tested may comprise bodily fluids or bodily fluid cells.

The culture media is specific for each substance to be tested and provides, for example, nutrient materials, serum, and/or antibiotic for cell culture. Some examples for media are: DMEM (Dulbecco's Modified Eagle Medium), Minimum Essential Media (MEM), example for serum is Fetal Bovine Serum (FBS) in addition to other biochemical needs for culturing each cell type.

Figure 2A:
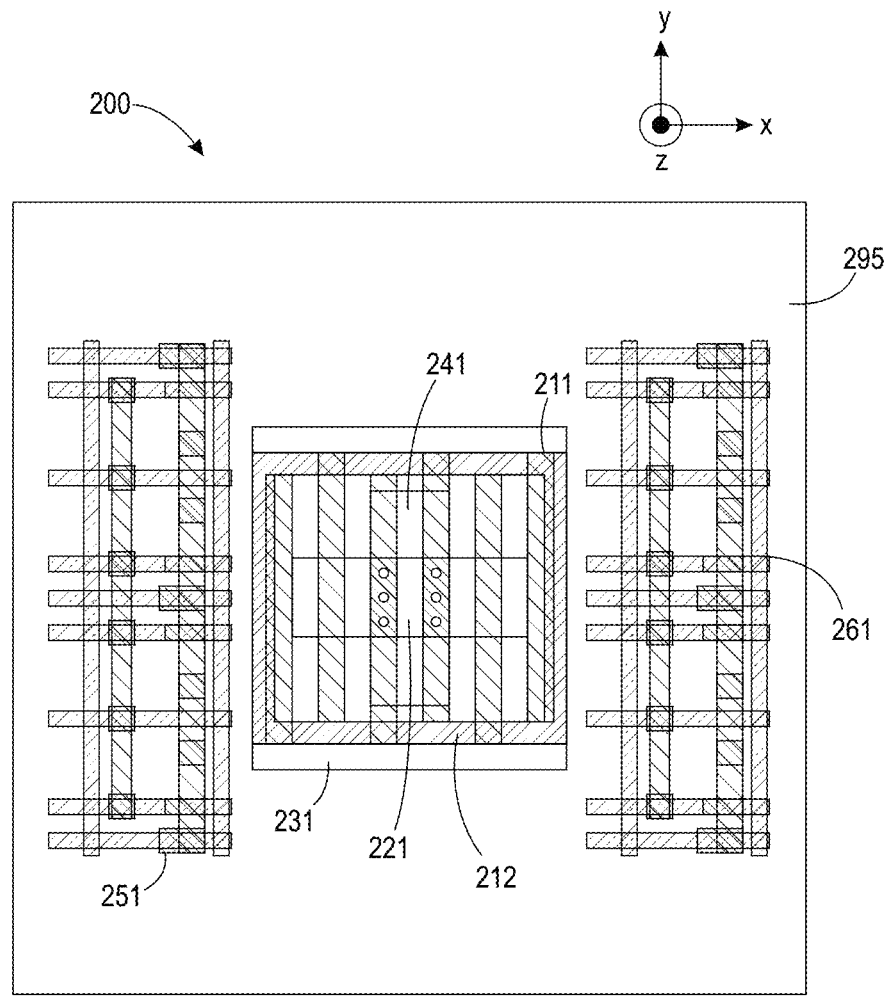
FIG. 2A is a top view of a portion of a backplane in the vicinity of a single pixel that includes the four subpixel sensors in accordance with some embodiments.
Figure 2B:
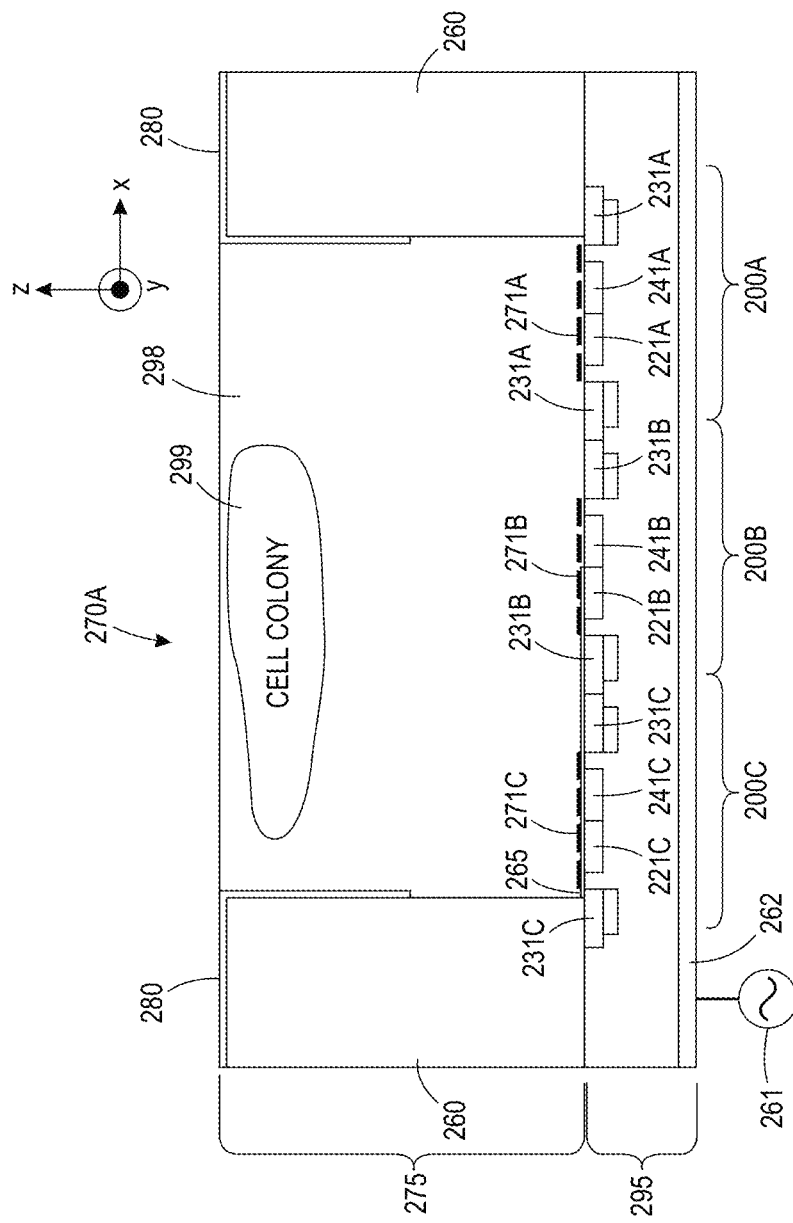
FIG. 2B is a side cross sectional view of a test well and a portion of a backplane of a test plate.
Figure 2C:
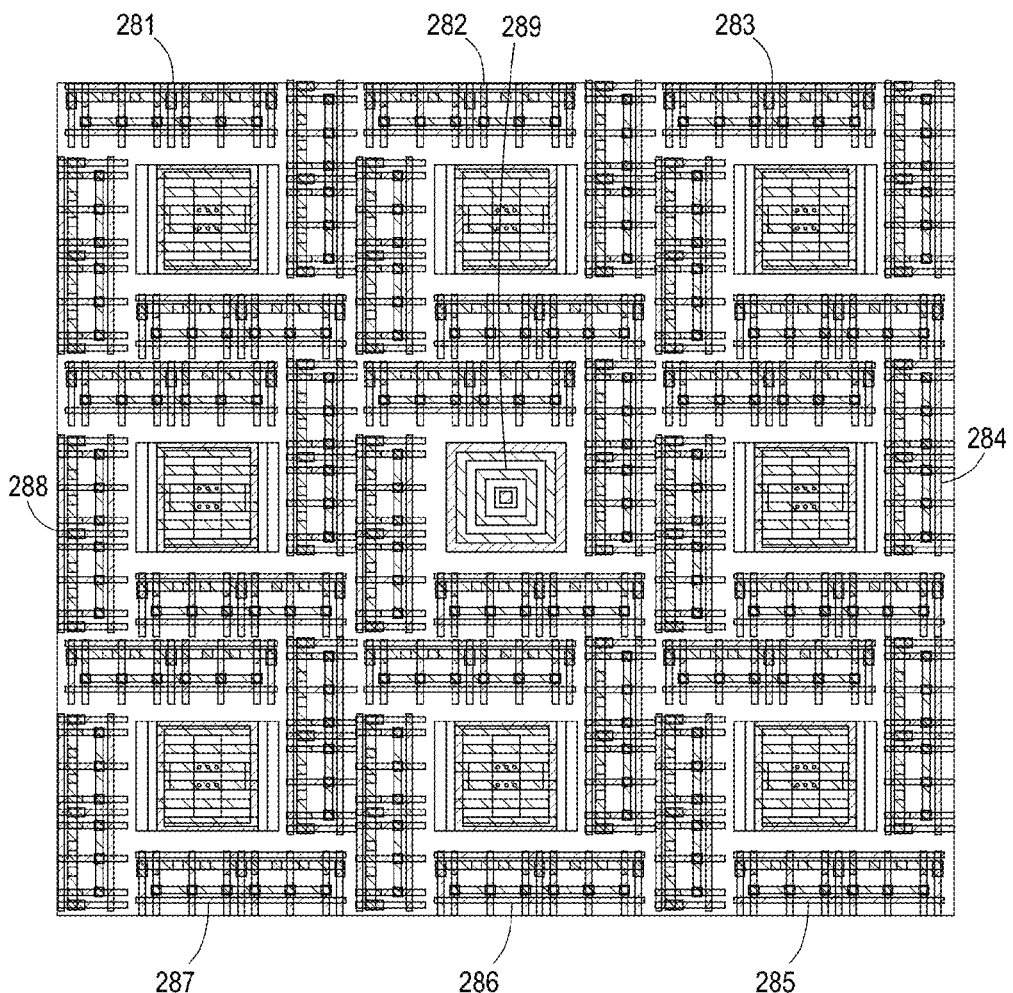
FIG. 2C is a top view of nine pixels that may be associated with one test well wherein one of the pixels includes an oxygen sensor in accordance with some embodiments.
Figure 2D:
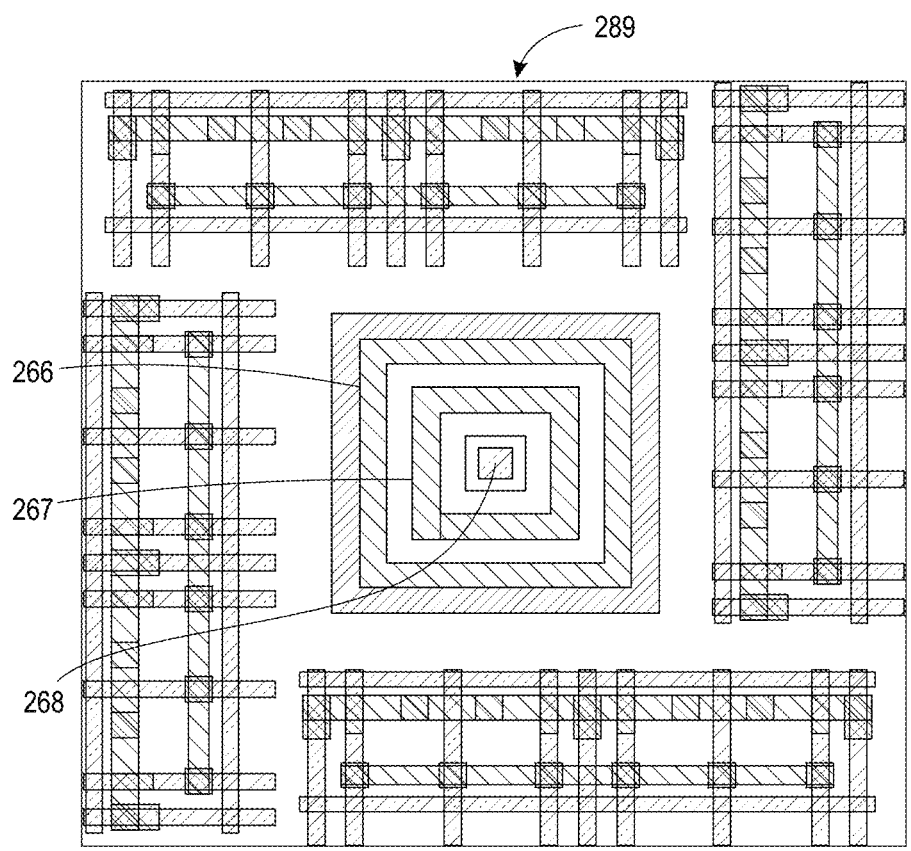
FIG. 2D provides a plan view of the oxygen sensor of FIG. 2C.
Figure 2F:
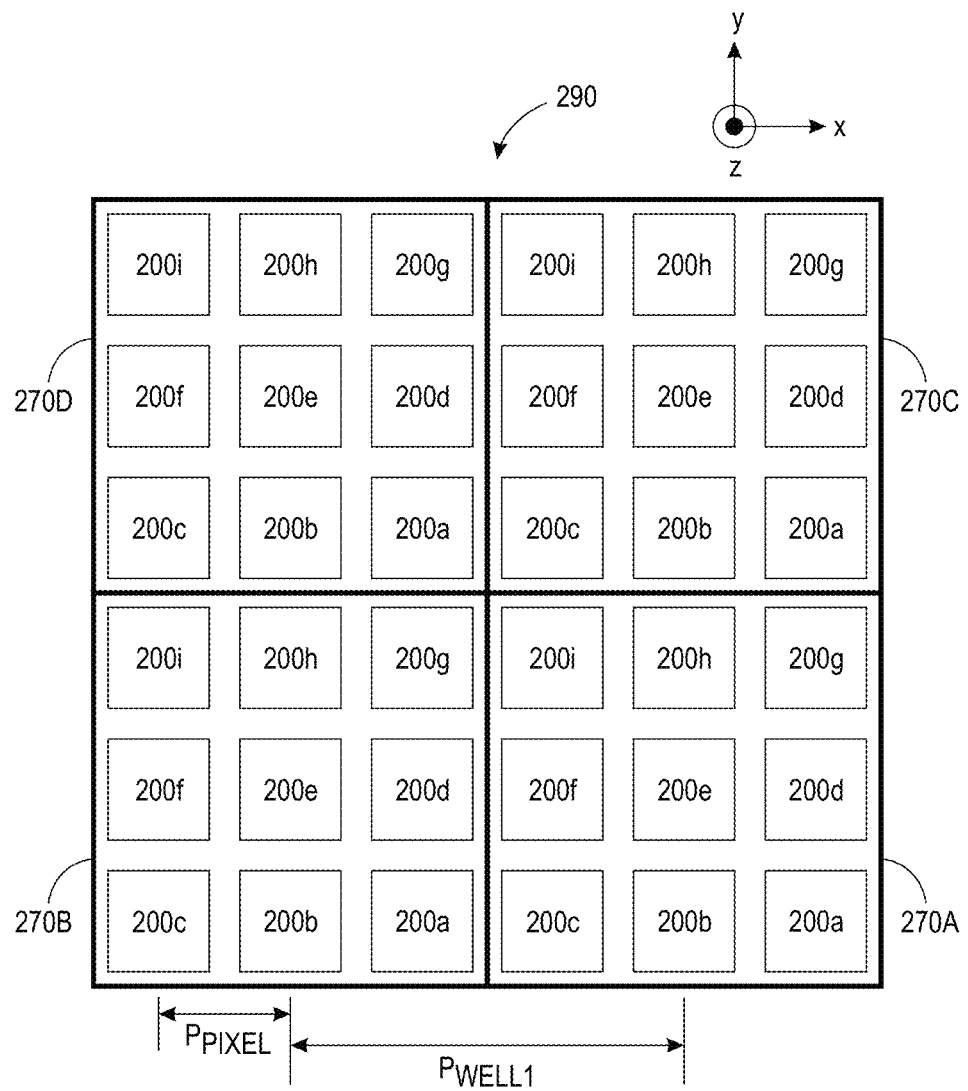
FIG. 2F is a top view of a portion of a test plate including the test well of FIG. 2B showing nine pixels in accordance with some embodiments.

In some embodiments, it is useful to have multiple, e.g., four, subpixel sensors per pixel, although more or fewer subpixel sensors are possible. The four subpixel sensors may include, for example, an impedance sensor, a chemical (pH) sensor, an acoustic sensor, and an optical sensor. FIG. 2A is a top view of a portion of a backplane 295 in the vicinity of a single pixel that includes the four subpixel sensors mentioned above. FIG. 2B is a side cross sectional view of a test well and a portion of a backplane 295 of a test plate 290. Test well 270a includes nine pixels, three of the nine pixels are shown in the cross section, each pixel having four subpixel sensors. FIG. 2F is a top view of a test plate 290 including the test well 270a of FIG. 2B showing nine pixels.

Referring now to FIG. 2A, pixel 200 includes four subpixel sensors disposed on the backplane 295. The sensors include an electrical sensor, e.g., such as an impedance sensor, a chemical sensor, an acoustic sensor, and an optical sensor. In this example, the impedance sensor includes interdigitated electrodes 211, 212 that facilitate sensing lateral impedance of the substance along the x, y, and/or z directions; the chemical sensor comprises a pH sensor and includes a pH sensing TFT 221; the acoustic sensor includes an integrated piezoelectric sensor 231 used in conjunction with a piezoelectric ultrasound transmitter 261 and piezoelectric film 262 shown in FIG. 2B; the optical sensor includes a light sensitive PIN diode 241. The pixel 200 also includes TFT circuitry 251 configured to facilitate access to the signals of selected sensors.

FIG. 2B shows a cross section of a portion of an electronic test plate including test well layer 275 and backplane 295. The test well layer 275 includes test well 270a that contains a substance to be analyzed, which in this example is a cell colony 299 growing in a 3D gel 298 which is the acellular environment around the cell colony 299. In this example, the test well 270a is associated with nine sensor pixels of the backplane 295 (see, FIG. 2C). FIG. 2B shows in cross section three sensor pixels 200a, 200b, 200c that each include four subpixel sensors similar to those of sensor pixel 200 discussed above. Each sensor pixel 200a, 200b, 200c, includes an impedance sensor, a pH sensor, an acoustic sensor, and an optical sensor. The impedance sensors of pixels 200a, 200b, 200c include interdigitated electrodes 271a, 271b, 271c, the pH sensors include pH sensing TFTs 221a, 221b, 221c; the acoustic sensors include an integrated piezoelectric sensor 231a, 231b, 231c used in conjunction with the piezoelectric film ultrasound transmitter 261 and piezoelectric film 262; the optical sensors includes light sensitive PIN diodes 241a, 241b, 241c. The test well 270a is defined by test well walls 260 that extend upward from the bottom surface 265 of the test well 270a. Disposed on and at least partially covering the surface of the walls 260 is a gold contact layer 280 which facilitates sensing impedance along the z direction. In some embodiments, the gold contact layer 280 can be used for the impedance sensors of one or of pixels 200a-c to sense impedance along the z direction.

As discussed above, an electrical impedance sensor suitable for use in an electronic test plate according to various embodiments can comprise interdigitated first and second electrodes disposed on the top surface of the backplane and exposed to the materials in the test well. The first and second interdigitated electrodes 211, 212 (see, FIGS. 2A and 2B) can be used to sense impedance laterally in the xy plane. The impedance sensor may also include the conductive contact layer, e.g., gold contact layer 280 as a third electrode. Each impedance sensor in the test well can sense vertical impedance between the first and third electrodes 211, 280 and/or between the second and third electrodes 212, 280. The arrangement of first, second, and third electrodes 211, 212, 280 as shown in FIGS. 2A and 2B provides for 3D sensing of electrical impedance along x, y, and z axes. Lateral and/or vertical electrical impedance sensing can be used to determine lateral and vertical electrical impedance spectrum, e.g., impedance as a function of frequency, $Z(\omega)$. The measured lateral and/or vertical electrical impedance may be used to determine cell count and/or cell viability. Upon cell death the cell membrane integrity, polarity, and cell morphology changes, and may result in different impedance values. It is expected that cell viability can be monitored by measurement of electrical impedance through the vertical electrodes or across the lateral interdigitated electrodes and viability correlated with the impedance changes. In some cases and for some cell types, a potential of 0.1 V can be applied and the impedance magnitude can be measured from 500 Hz to 10 kHz. In some cases, the detection limits and dynamic range include sensitivity of |Z|<50 Ohms and θ~0.50 within frequency range of 1 KHz to 1 MHz.

A chemical pH sensor suitable for use in an electronic test plate according to various embodiments can comprise an ion sensitive silicon nitride gate of a thin film transistor. Such a sensor can be used to measure extracellular pH value, for example. In some cases, the pH sensor can be fabricated to have a sensitivity range of between 0.05 to 0.1 pH, a range of 4.0-8.0 pH, and a response time less than one minute.

An acoustic emitter/sensor 262 in the test wells of the electronic test plate according to various embodiments can provide 3D acoustic sensing of the substance in the test well. A suitable acoustic emitter/sensor may comprise a thin film piezoelectric sensor, e.g., made of the material polyvinylidene fluoride (PVDF), or electrostrictive capacitive, e.g. made of metallized silicone, that is shaped around the pixel. The piezoelectric emitter/sensor is configured to sense waves generated by a piezoelectric emitter 261 and piezoelectric film 262. For example, in some configurations, a piezoelectric film transmitter generates a pulsed ultrasonic wave that is reflected (echoes) from the interface between the cell colony 299 and the 3D gel 298. The piezoelectric sensor senses the reflected wave by amplifying the time-delayed echo using an amplifier (not shown) connected to transducer 262. Time of flight techniques for the acoustic sensing may be used to determine the position of the cell/gel interface. By comparing a first position of the cell-gel interface detected at time, $t_1$, to a second position of the cell-gel interface detected at a later time, $t_2$, characteristics of the motility of the cell culture, e.g., existence of motility, velocity, and/or acceleration, etc., can be determined. Cell motility may be induced by generating chemical gradient and or adding chemo-attractant at a distance from cells. The acoustic sensor may provide 100 μm-1 cm z-axis penetration with +/−100 μm z-position sensitivity, 100 nsec pulse echo resolution at 1-30 MHz operating frequency. For example, in some embodiments, acoustic probing can be used with pulse-echo timing to continuously measure the vertical cell colony position.

An optical detector suitable for an electronic test plate in accordance with various embodiments comprises at least one thin film PIN diode the arranged on the backplane and at the bottom of a test well. In some embodiments, multiple thin film PIN diodes may be used per pixel, e.g., about 4 arranged in an array. The optical detectors are configured to sense light generated by a light source arranged to emit light through the substance to be tested, e.g., from the top surface or bottom surface of the test plate. As the light traverses through the test well, the light interacts with materials within the test well. For example, the light emitted by the source may be absorbed, scattered and/or reflected by the cells and/or tissue structures. The light that has interacted with the materials in the test well is sensed by the optical detectors and can be used to determine the cell optical density, from which cell count can be determined. Additionally, the signal of the optical sensor may be used to determine lateral cell motility by comparing a light detected at a first time to light detected at a second, later time. In some embodiments, the thin film PIN diode detectors may have a sensitivity on the order of about 3000 photons, a range of $10^4$ to about $10^8$ photons, although other sensor sensitivities are possible using different illumination sources. In some implementations, the detectors may have a response time of less than about 100 μsec.

In some embodiments, one or more oxygen sensors may be associated with a test well. It may be used to identify hypoxic cancer cells or hypoxia in their environments. Hypoxic and acidic conditions are associated with increased mutations, chromosal instability, spontaneous transformation, resistance to apoptosis, and increased invasion and metastasis of cells. FIG. 2C is a top view of nine pixels 281-289 that may be associated with one test well. Pixels 281-288 are similar to pixel 200 illustrated in FIG. 2A with four subpixels as previously described. Pixel 289 comprises a dissolved oxygen sensor 252 which is illustrated in more detail in the plan view of FIG. 2D and in FIG. 2E which is a diagram showing pixels 288, 289, and 284 in cross section. In some embodiments, the oxygen sensor 289 may be based on a proton exchange membrane, such as Nafion. Nafion is a type of proton exchange membrane (also referred to as a polymer electrolyte membrane) (PEM) which is semipermeable and designed to conduct protons (H+). Nafion is commercially available from Dupont in a thin-film format. When implemented as an oxygen sensor in test wells, Nafion, or other type of solid electrolyte 253 can be coated or heat-sealed onto the electrodes 266-268 in the well, with an oxygen permeable membrane 252 (e.g. PTFE) coated on top of the solid electrolyte 253. The electrodes of the oxygen sensor include a reference electrode 266, working electrode 267, and a counter electrode 268. The dissolved O2 in the cell culture matrix permeates through the oxygen permeable membrane 252 to the solid electrolyte 253, e.g., Nafion, where the O2 undergoes a reduction reaction (i.e. O2+4H++4e- -->2H2O). This reduction reaction current is measured by the working 267 and counter electrodes 268 and the voltage between the reference electrode 268 and the working electrode 267 is also measured.

FIG. 2F shows a top view of a portion of an electronic test plate 290 that includes the test well 270a of FIG. 2B along with identical test wells 270b, 270c, and 270d. The backplane 295 includes a repeating pattern of identical sensor pixels 200a-200i. Each sensor pixel 200a-200i may include, for example, four subpixel sensors. In this example, each test well 270a-270d comprises 9 sensor pixels and 36 sensor subpixels. It will be appreciated that this configuration is provided for illustrative purposes and that electronic test plates with more or fewer test wells associated with more or fewer pixels and subpixels are possible.

Figure 2G:
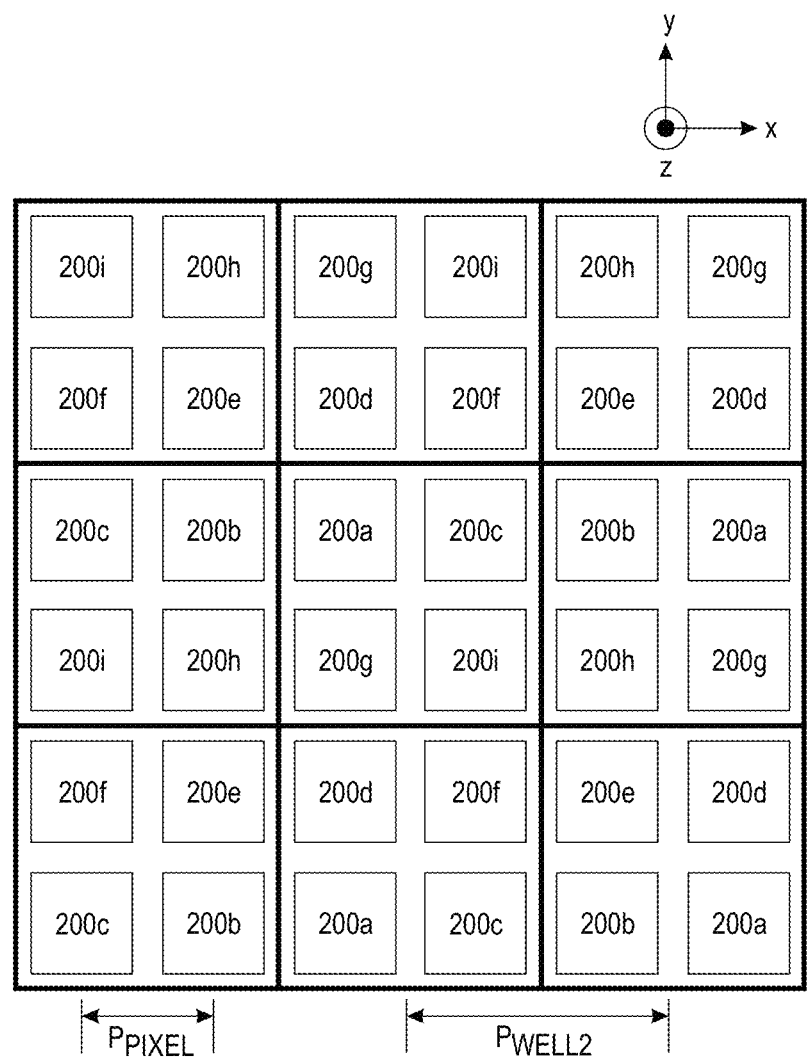
FIG. 2G illustrates a top view of a backplane and test plate having a test well pitch that is larger than the backplane pixel pitch.
Figure 2H:
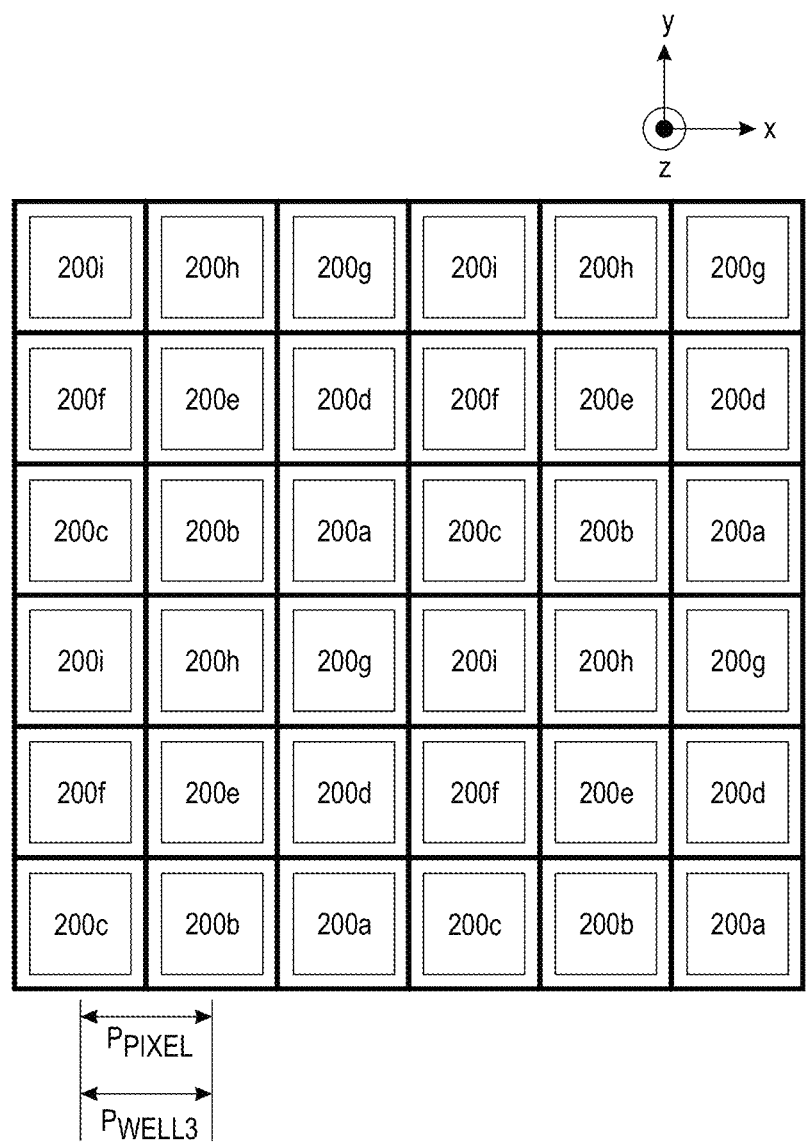
FIG. 2H illustrates a backplane having a pixel pitch that is equal to the test well pitch.

As illustrated in FIG. 2F, the test plate has a test well pitch, $P_{well1}$, which is the center-to-center distance between test wells. The backplane has a pixel pitch, $P_{pixel}$, which is the center-to-center distance between pixels. As shown in FIGS. 2F-2H, the pitch of the test wells on the test plate may be different from or the same as the pitch of the sensor pixels of the backplane. FIG. 2F illustrates the top view of a backplane having a pixel pitch, $P_{pixel}$, that is smaller than the test well pitch, $P_{well1}$, wherein each test well includes 9 sensor pixels. FIG. 2G illustrates a top view of the same backplane with a test plate having a test well pitch, $P_{well2}$, that is smaller than $P_{well1}$, and larger than the backplane pitch, $P_{pixel}$, wherein each test well includes 4 sensors. FIG. 2H illustrates the same backplane having a pixel pitch, $P_{pixel}$, that is equal to the test well pitch, $P_{well3}$ wherein each test well includes one sensor pixel. It will be appreciated that an electronic test plate need not have a constant pixel pitch or a constant test well pitch across the entire test plate. In some embodiments, an electronic test plate can include a backplane that includes sensor pixels arranged with a number of different pixel pitches and the test wells on the test plate can also include a number of different test well pitches. The test well width dimension can vary from traditional large wells (e.g. 5 mm) down to well width dimensions of several hundred microns while using the same TFT backplane. For example using larger wells, e.g., 5 mm diameter wells, with 300 µm pitch polysensing pixels would result in a larger number polysensing pixels per well when compared to the number of pixels per wells when using smaller wells, e.g., 400 µm diameter wells with 300 µm pitch polysensing pixels.

In some embodiments, test well structures can be made either directly on top of the TFT backplane, e.g., using patterned plastics, forming a unitary electronic test plate. In some embodiments, the test plate and backplane can be fabricated as separate structures after which the test plate is bonded to the TFT backplane.

Figure 3A:
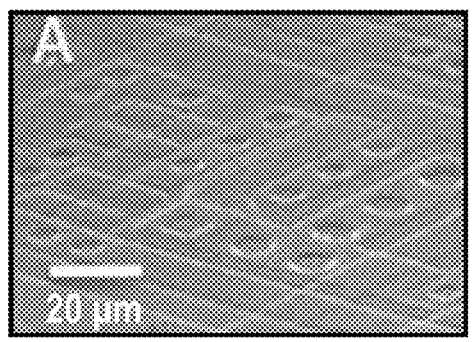
FIGS. 3A-3D are photographs of electronic test plate prototypes fabricated using different well sizes and materials in accordance with various embodiments.
Figure 3B:
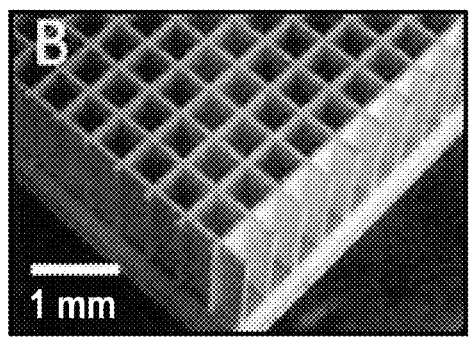
Figure 3C:
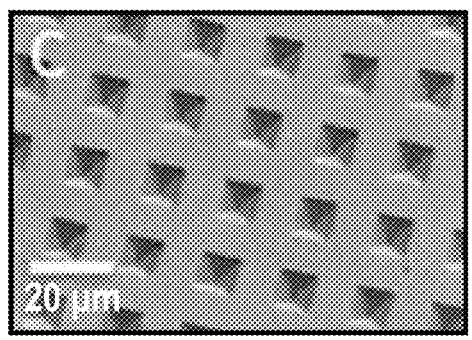
Figure 3D:
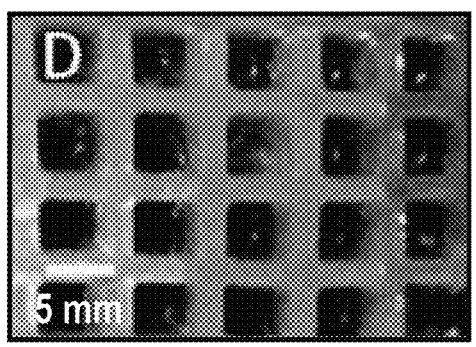

FIGS. 3A-3D are photographs of electronic test plate prototypes that were fabricated using different well sizes and materials. FIG. 3A demonstrates the ability to fabricate 90 µm polysensing pixel circuits on a TFT backplane. FIG. 3B illustrates the use of SU-8 photoresist for fabrication of high aspect ratio wells. FIG. 3C is a photograph of 10 µm Si microwells that were fabricated. FIG. 3D is a photograph of 5 mm hydrogel test wells that could be readily loaded with 3D laminin rich gels via hand pipetting, and retained viable cells up to 8 days of 3D embedded culture. In some designs glass and/or injection molded plastic may be used instead of Si to form the test wells, the glass or plastic providing enhanced stability of the cell walls.

Gel and cell loading into that test wells can be achieved by pipetting or passivating the Au regions (upper and sidewalls) with biocompatible coatings like PEG-thiols and activating the bottom of wells with laminin rich gels (via dipping into gel solution at 4° C. and spin coating at 37° C. prior to exposure to cell solution). In some embodiments the gel can formed in situ inside wells via polymerization. Selective delivery of gel, cell, or cell culture media can be evaluated by optical microscopy.

Figure 3E:
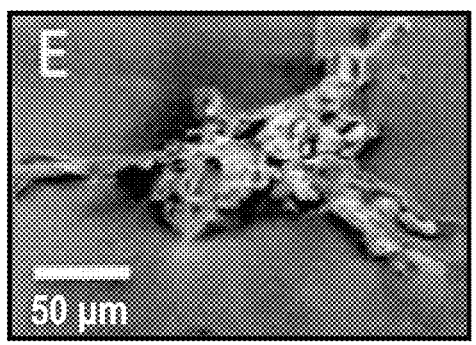
FIGS. 3E and 3F show exemplary 3D cultures of MDA-MB-231 cancer cells over thin gold coated glass slides and silicon, respectively.
Figure 3F:
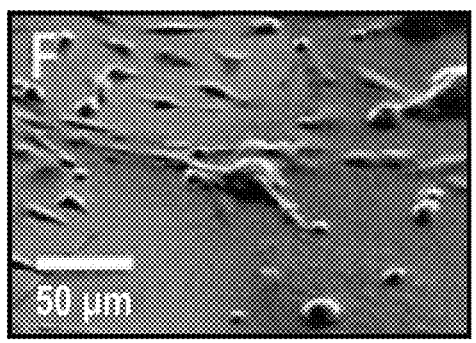

FIGS. 3E and 3F show exemplary 3D cultures of MDA-MB-231 cells over thin gold coated glass slides and silicon, respectively, indicating higher growth and formation of stellate structure on gold.

Figure 4A:
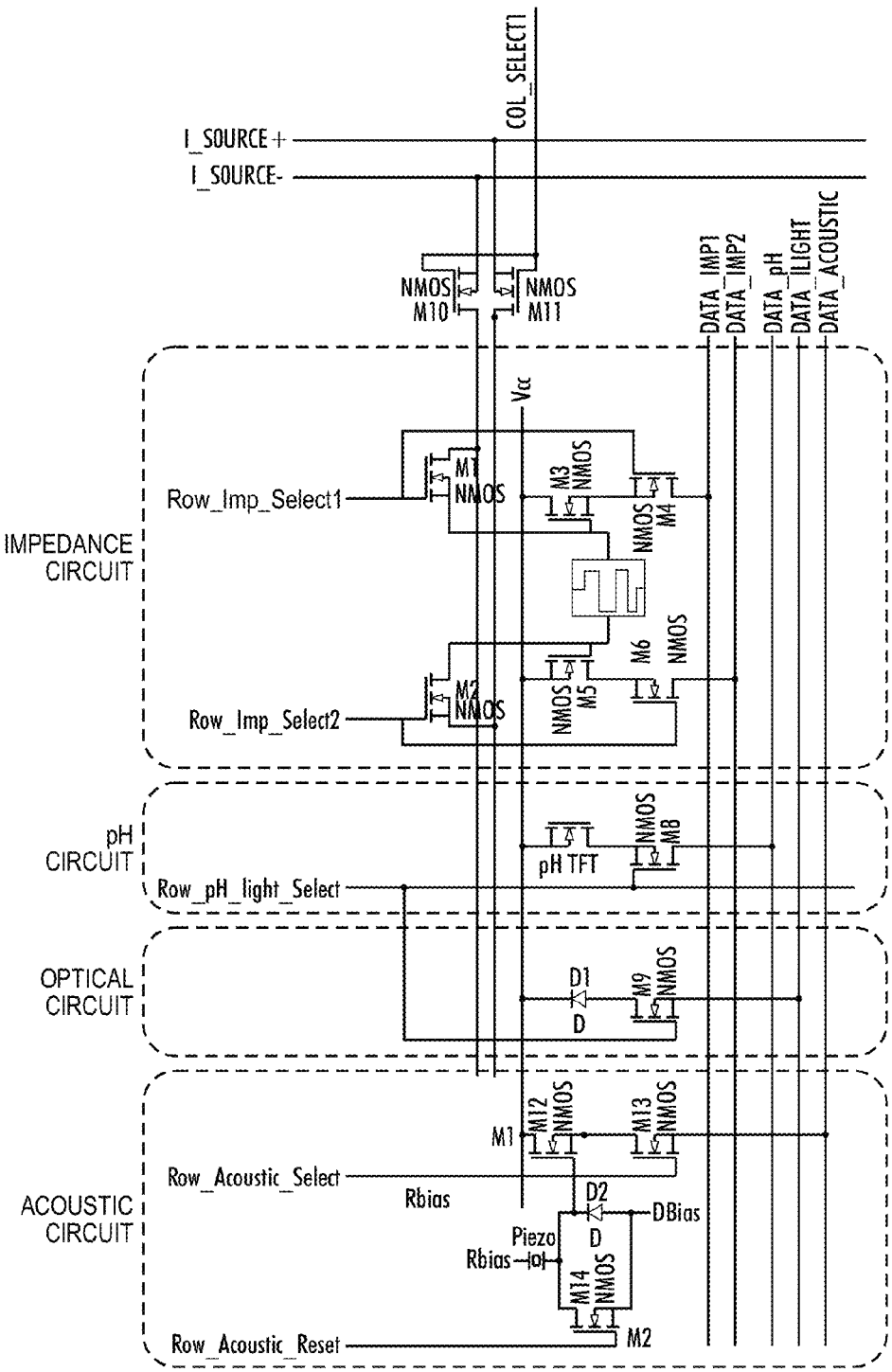
FIG. 4A provides a schematic for exemplary TFT subpixel sensing circuits and sensor select circuitry that can be implemented to provide senor signals from the impedance, pH, optical, and acoustic sensors in accordance with some embodiments.

FIG. 4A provides a schematic for exemplary TFT sub-pixel sensing circuits and sensor select circuitry that can be implemented to provide senor signals from the impedance, pH, optical, and acoustic sensors. In this example, the exemplary sensor select circuitry for the polysensing pixel has five interrogation functions: vertical electrical impedance, lateral electrical impedance, local pH sensing, optical intensity, and acoustic response.

To interrogate vertical electrical impedance, either Row_Imp_Select1 or Row_Imp_Select2 can be selected e.g., by raising the voltage on these lines from off state, to turn-on voltage (the off state may be about 5 V and the turn-on voltage may be about +15V, for example). Raising the voltage on these lines turns on transistors M4 or M6. One of the interdigitated electrodes is electrically connected to the external current source through M1 or M2 and column source lines I_Source+ or I_Source−. The current flows through the electrode, the interrogating cell and the common electrode plane (e.g., gold contact layer 280 shown in FIG. 2B). The voltage of the sensing electrode will be sampled and buffered by the readout source follower TFT (M3 or M5) and the signal will appear on data line (Data_Imp1 or Data_Imp2). I_source+ and I_source− can be be controlled by external function generator to provide amplitude and frequency sweeping function. Since the electrode potential is buffered and amplified by the source follower M3 or M5, signal degradation and cross talk between neighboring pixels can be small, e.g., may be reduced to a negligible amount. Lock-in amplifier can also be used for excitation (I_Source) and readout (Data_Imp) to further reduce noise and interference, and improve sensitivity.

To interrogate lateral impedance, both Row_Imp_Select1 and Row_Imp_Select2 are turned on simultaneously, which turns on transistors M4 and M6. Excitation current will then be flowing through TFT M1 to electrode, cell, electrode, TFT M2 and then I_source−. The voltage difference between the two interdigitated electrodes will be buffered by M5 and M3, and readout through transistors M4 and M6. The lateral impedance signal will appear on data lines Data_Imp1 and Data_Imp2.

The local pH value can be sensed by an ion sensitive field effect thin film transistor (pH TFT) which measures ion concentration, such as concentration of $H^+$ in solution. The current through the transistor changes as a function of ion concentration. To readout the pH signal on the Data_pH line, TFT M8 will be turned on by Row_pH_light_Select while the other Row selects are kept off.

An integrated light sensitive PIN diode D1 can be used to monitor the well opacity. To readout the light level at well bottom, the Row_pH_light_Select line will turn on TFT M9 and the photo current can be readout at the Data_light signal line. Light sensitivity of these PIN photo sensors can be very good and largely depends on the external readout amplifiers. In a well-engineered system, working under integration mode, light sensitivity of a few thousand visible photons can be demonstrated.

Acoustic sensing can be achieved using a piezoelectric sensor, (labeled Piezo in FIG. 4A) and mixer diode D2 connected to a bias voltage, DBias. The piezo transmitter (see, elements 261 and 262 of FIG. 2B) emits an acoustic, e.g., ultrasonic, pulse that interacts with the structures and/or other materials in the test well. The interaction may dampen and/or otherwise modify characteristics of the pulse as it travels through and/or around the structures and/or materials. The piezoelectric sensor senses the modified acoustic pulse and generates an electrical signal in response.

Before data acquisition, charges present on the piezoelectric transducer and/or elsewhere are cleared by activating transistor M2. Then, the DC component of the Rbias Waveform (Dbias) biases the diode D2 at a particular range gate, where the nonlinear nature of the diode D2 acts as a mixer. This mixes the received ultrasound signal by the Rbias sinusoidal reference signal or a reference signal shifted by 90 degrees in the in-phase and quadrature components. After mixing, the resulting current is integrated on the receiver capacitance over a time that is longer than, such as an integer multiple of, the period of the carrier frequency. This integrated signal is proportional to the real and imaginary components of the baseband received signal that contains information about the reflectivity of the environment at a certain range gate. These in-phase (I) and quadrature (Q) values can be read off on the Data_acoustic line when the Row_acoustic_select is activated.

The acoustic sensor may be used to determine acoustic impedance of the substance by sweeping the frequency, phase, and/or amplitude of the transmitted acoustic signal and sensing the resulting acoustic wave using the acoustic sensor. In some implementations, time-of-flight of the transmitted acoustic signal may be determined.

Additional information regarding acoustic sensing which is applicable to the embodiments discussed herein is provided in commonly owned U.S. Patent Publication 20130235698 which is incorporated herein by reference.

Figure 4B:
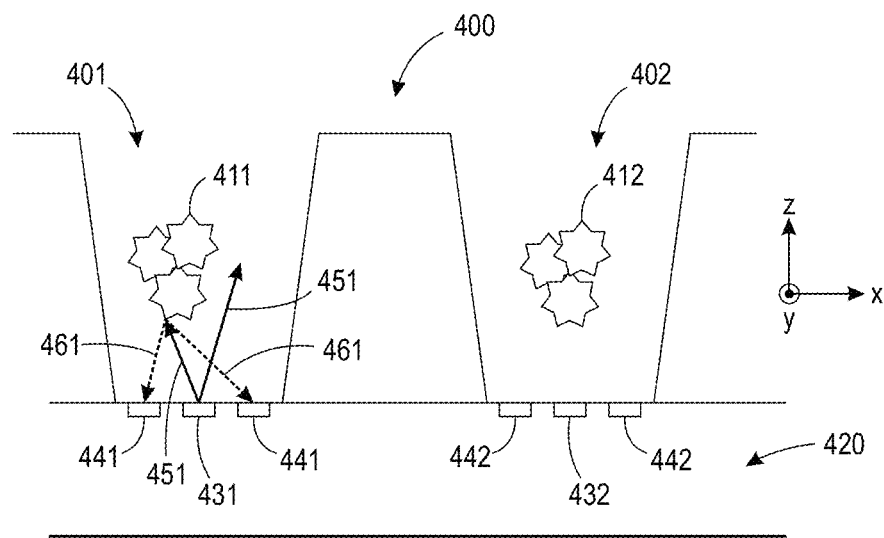
FIGS. 4B through 4D show configurations for providing input light for optical sensing in accordance with various embodiments.
Figure 4C:
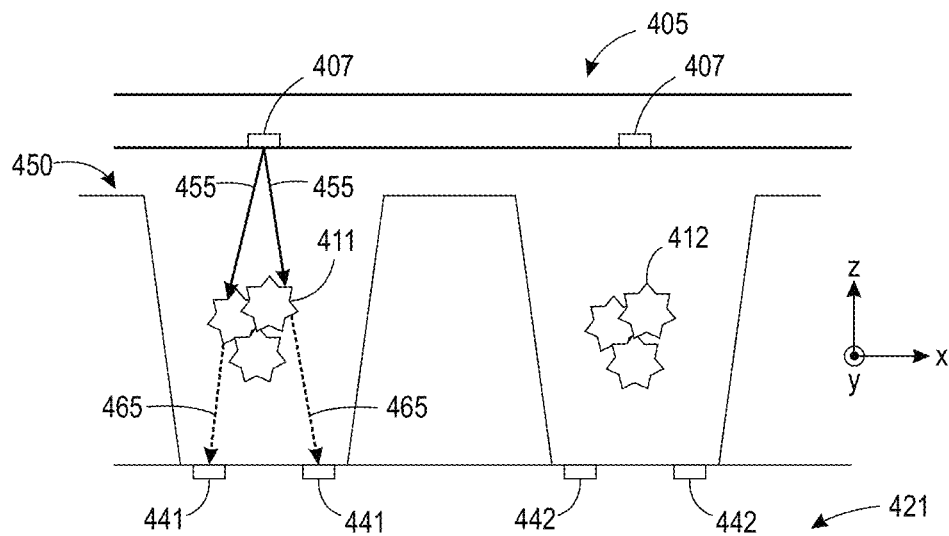
Figure 4D:
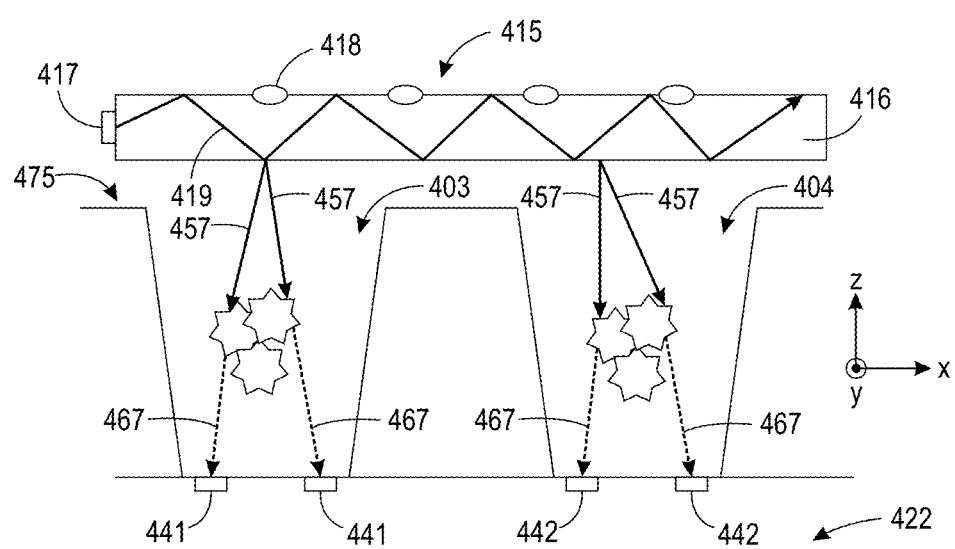

The input light source used for optical sensing can be disposed above or below the test wells and can provide input light having a controlled spectrum, pulse width, intensity, and/or collimation. FIGS. 4B through 4D illustrate a few configurations that may be used to supply the input light, although other configurations are also possible.

FIG. 4B shows a portion of an electronic test plate 400 including test wells 401, 402 containing a substance to be analyzed 411, 412. Backplane 420 is arranged along the bottom of the test wells 401, 402. Each test well 411, 412 is associated with one or more light emitting devices 431, 432, e.g. photodiodes disposed on the backplane 420, and one or more optical sensors 441, 442. Each light emitting device 431, 432 can be energized by the sensor select circuitry in synchrony with selection of the optical sensors 441, 442 to provide optical sensing for the pixel or pixel group. For example, the substance to be analyzed 411 may reflect at least a portion of the input light 451 emitted by the light emitting device 431. The optical sensors 441 sense the reflected light 461 and generate an electrical signal in response.

In some embodiments the input light source for optical sensing may comprise a source separate from the backplane that provides the input light from above or below the test wells. For example, in some configurations, the input light source may be located above the test wells as shown in FIGS. 4C and 4D. The input light source may provide pixelated light (illustrated in FIG. 4C) or nonpixelated light (illustrated in FIG. 4D). FIG. 4C depicts and input light source 405 disposed above the test wells 408, 409 of electronic test plate 450. In this example, the light source 405 provides pixelated light using an array light emitting devices 407, 408 that can be separately turned on and off to provide input light to each well 408, 409 individually. The substance to be analyzed 411 may block (absorb and/or reflect) a portion of the input light 455. At least a portion of the light 455 emitted by the light emitting device 407 is transmitted to the optical sensors 441 which sense the transmitted light 465 and generate an electrical signal in response. In some embodiments, the pixelated light source may be accomplished using digital light projector (DLP) or a projector and mirror combination wherein the mirror reflects light from the projector into a particular test well or group of test wells. The mirror can be attached to a movement mechanism configured to move the mirror along x and/or y directions to provide the input light for the test wells.

In some embodiments, as shown in FIG. 4D, input light may be provided to the electronic test plate by a light source 415 comprising one or more light emitting devices 417 and a waveguide or light pipe 416. In the example of FIG. 4D, the input light source 415 is located above the test wells 403, 404. The light emitting device 417 is optically coupled to the waveguide 416 at one or more input edges of the waveguide 416. Light 419 emitted by the light emitting device 417 travels along the waveguide 416 by total internal reflection (TIR). Optionally, the waveguide 416 may be wedge shaped or may include extraction features 418 that extract the input light 457 towards the test wells 403, 404. Optionally, one or more optical films may be disposed on the waveguide to collimate the input or otherwise change the angle of the input light. At least a portion of the input light 457 is transmitted to the optical sensors 441 which sense the transmitted light 467 and generate an electrical signal in response. Although FIG. 4D shows the waveguide disposed over the test wells, in alternative configurations, the waveguide and light emitting devices may be disposed below the test wells, e.g., on the backplane.

Figure 5A:
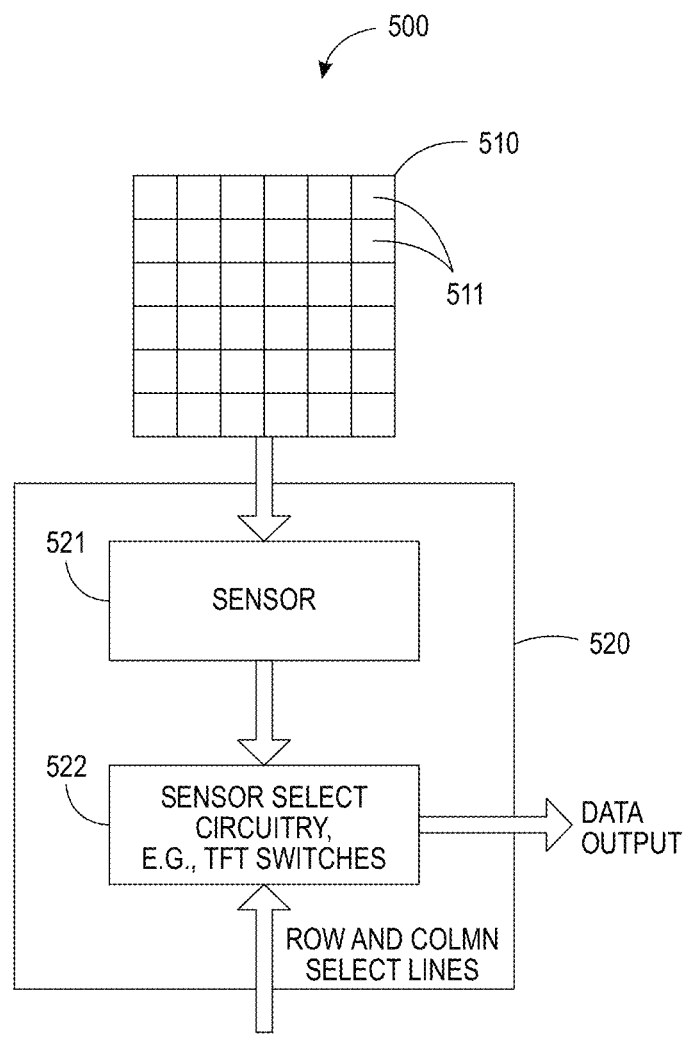
FIG. 5A is a block diagram of an electronic test plate 500 according to some embodiments.

FIG. 5A is a block diagram of an electronic test plate 500 according to some embodiments. The electronic test plate 500 includes a test plate 510 comprising test wells 511. The electronic test plate 500 also includes a backplane 520 comprising sensors 521 arranged relative to the test wells 511 so that multiple sensors 521 are associated with each test well 511. The backplane includes sensor select circuitry 522, e.g., comprising TFT switches, that provides signals from selected sensors on parallel data outputs. The sensor select circuitry can be controlled by row and column select lines and may provide simultaneous access to multiple sensor signals in parallel.

Figure 5B:
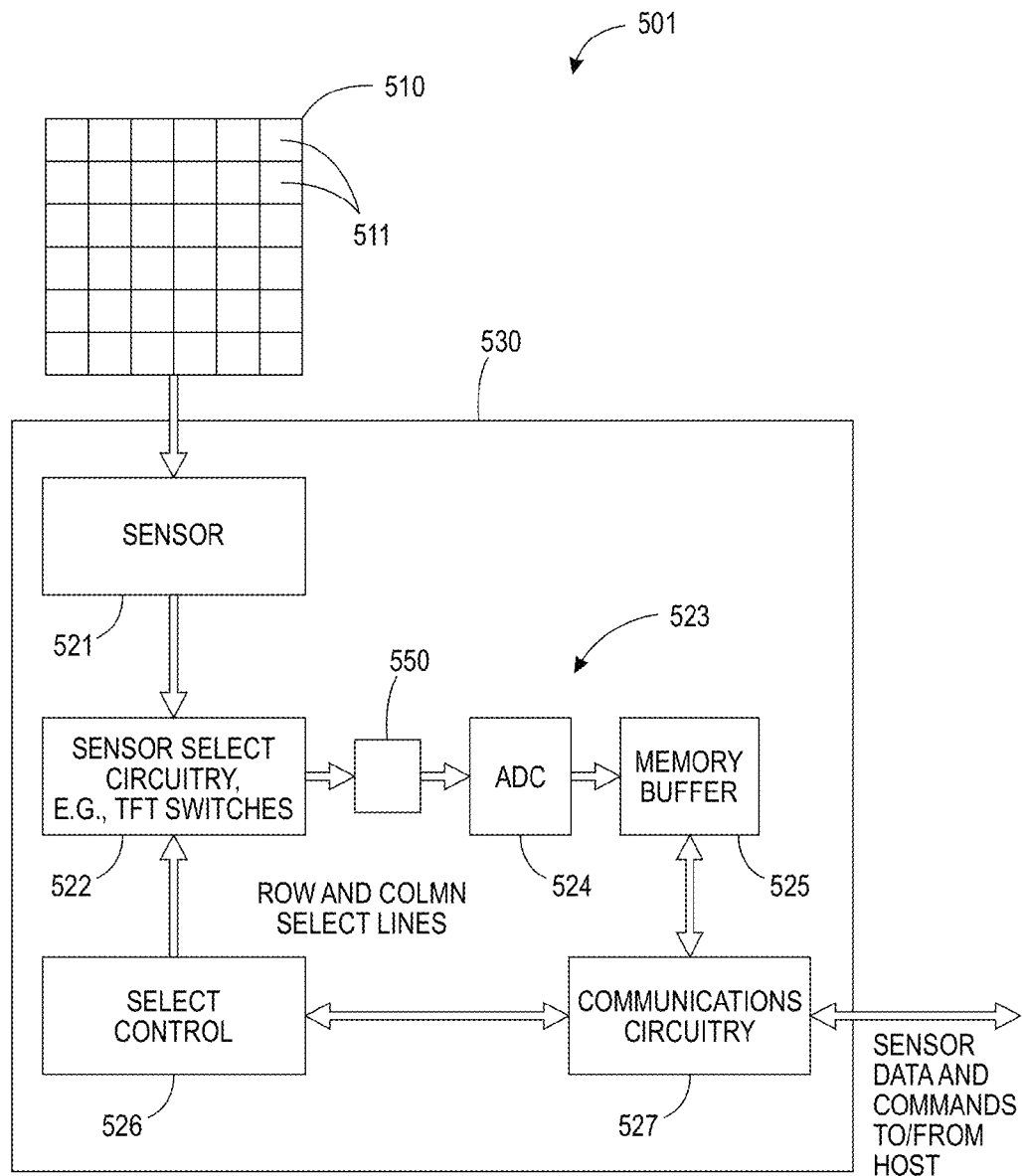
FIG. 5B is a block diagram of an electronic test plate that is similar in some respects to the electronic test plate of FIG. 5A and includes additional optional features in accordance with some embodiments.

FIG. 5B is a block diagram of an electronic test plate 501 that is similar in some respects to the test plate 500 of FIG. 5A. The backplane 530 of test plate 501 includes additional optional features. The electronic test plate 501 additionally includes readout circuitry 523 configured to receive sensor signals of the selected sensors. The readout circuitry 523 may optionally include signal processing circuitry 550, e.g., filters, amplifiers, etc., configured to condition the sensor signals. For example, the signal processing circuitry may include one or more differential amplifiers configured to enhance the signal to noise ratio (SNR) of the sensor signals. In some embodiments, the readout circuitry may include analog to digital converter (ADC) 524 configured to convert analog sensor signals to digital sensor signals. Optionally, the readout circuitry 523 may temporarily store the digital sensor signals in a memory buffer 525. In some implementations, the backplane 530 includes select control circuitry 526 that generates the row and column select lines, e.g., in accordance with commands received from a host processor. The electronic test plate 501 includes communication circuitry 527 configured to receive commands from a host processor and/or to transfer the digital sensor signals to the host processor. For example, the commands from the host may include instructions regarding which sensors should be accessed and/or the frequency of access; these and other parameter may be selected by a user through a user interface running on the host processor, for example. The communications circuitry 527 and the host processor can be configured to communicate commands and/or data via a standard communications protocol such as Universal Serial Bus, IEEE 1394, ISO/IEEE 11073 or other communications protocol.

Figure 6:
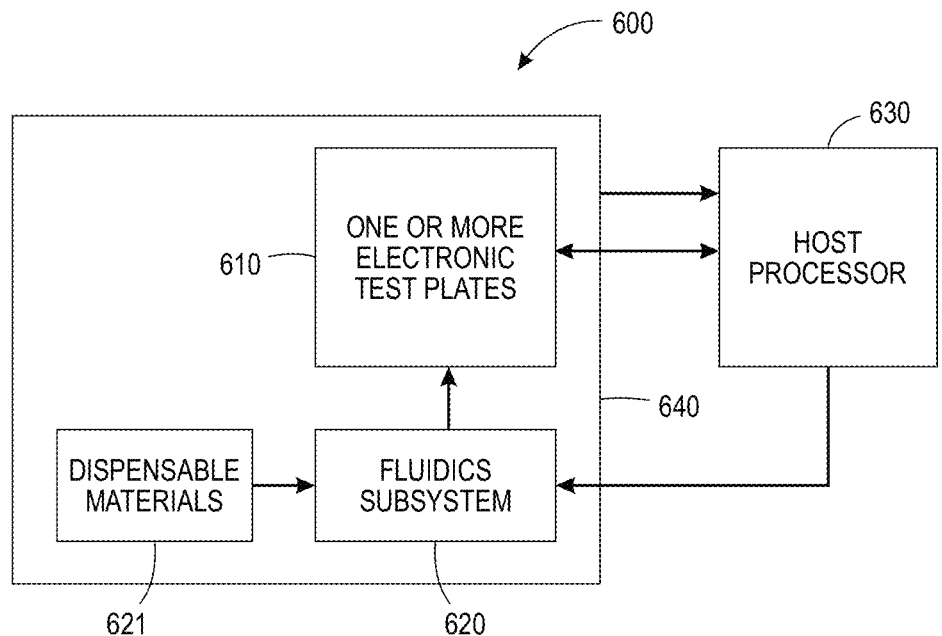
FIG. 6 is a block diagram of a test system that incorporates one of more of the electronic test plates in accordance with embodiments described herein.

In some embodiments one or more electronic test plates 610 as described above can be incorporated into a test system 600 as shown in the block diagram of FIG. 6. The test system 600 includes a fluidics subsystem 620 configured to dispense materials into and/or withdraw materials from into the test wells of the electronic test plates 610. In some configurations, the fluidics subsystem may comprise a printer, and/or other device configured to position substances to be analyzed into the test wells. In some embodiments, the fluidics subsystem may comprise pipettor apparatus configured to automatically dispense and/or withdraw materials from the test wells under the command of a controller, e.g., the host processor.

The fluidics subsystem may comprise a functional film on the test plate that is configured to guide loading of the reagents into the wells via dip coating. For example, gel and cell loading into that test wells can be achieved by passivating the Au regions (upper and sidewalls) with PEG-thiols. Alternatively or additionally, the fluidics subsystem may include a chemical or physical surface modification of a test plate that is configured to provide adherence of the substance to be analyzed to the wells. For example, the surface modification may involve activating the bottom of wells with laminin rich gels (via dipping into gel solution at 4° C., spin coating under vacuum, heating at 37° C. to yield a gel layer of 500 µm prior to exposure to cell solution). Cells are suspended in liquid phase gels at 4° C. then seeded into the gel coated wells. After the gel is allowed to solidify, media is added and cells are allowed to adhere. Non-adherent cells are washed away prior to 48 hrs of culture. Selective delivery of gels, cells, cell culture media and/or chemoattractants and labels can be evaluated by optical microscopy.

In some configurations, surface molecular engineering for the test plate can involve reacting the test plate substrate with piranha solution (hydrogen peroxide/sulfuric acid 2:5 v/v) at 70-80° C. or with Nanostrip 2X (Cyantek, Fremont, Calif.) at room temperature, and drying under nitrogen, resulting in a clean surface devoid of organic residues (e.g. gold) and a hydroxyl layer with contact angle of almost 10 degrees on silicon. The gold may be first modified with a 20 mM mixture of alkane thiols of 11-MUA and 3-MPA (1:10 v/v) for 16 h to create a self-assembled monolayer (SAM) and then exposed, for 30 min, to a mixture of 30 mM NHS and 150 mM EDAC esters. The substrate with NHS on gold may be sterilized with 70% ethanol for 15 min, and then exposed to fibronectin for 45 min in a phosphate buffer solution (PBS) with a concentration of 0.1 mg/ml at room temperature. To remove loosely bound moieties from the surface after each step of the surface modification, the substrate can be rinsed with its original solvent and deionized (DI) water, respectively. As a result, the immobilized fibronectin forms a robust cell-adhesive biocompatible layer on the gold.

In some configurations, surface modification is performed on each well to improve cells attachment and seeding cells in certain area through chemical formation of films that promote cell adhesion because of carrying biomolecules such as vitronectin, laminin, and cluster designation 44 (CD44) proteins or peptide mimetics, as well as glycan, glycosaminoglycan, and fat. Sensor surfaces can be functionalized biochemically with extracellular tissue components or altered physically to generate surface topography that influence cell function in a targeted way. For instance 3D gels can be made from Hyaluronan molecules that enrich invasive cell subpopulation in a pool of cancer cells thus affecting the sensor signals. Nanomaterials (e.g. nano-wires, nanoparticles, nanotubes, nanorods with or without biologically targeted moieties) can be used on the surface of the test plate and/or in the 3D gels to improve a host of parameters such as gel adhesion, cellular function, mechanical scaffolding, and ultimately signal to noise ratio.

In some embodiments, hybrid matrices may be formed. These hybrid matrices may include at least one of nanomaterials and thermoresponisve 3D gels. The matrix components can be premixed with certain ratio and get delivered into each well by pipette, channel or printer nozzle. Alternatively, the matrix components can be delivered through different nozzles and get mixed in each well. The fluidics subsystem may be arranged to provide the capability of changing and tuning the properties of matrices for each cell type. In some scenarios, mechanically robust metal particles or rods may be added to tune the property of matrix according to the different cell types. In some scenarios, the gel may be premixed with nanomaterials to induce different properties.

In some embodiments, one or more of the electronic test plates and/or the fluidics subsystem may interface with a host processor 630. In some configurations, the host processor 630 can control the dispensing and/or withdrawing of materials into/from the test wells as well as the controlling the type of substance characteristics sensed and/or the frequency of sensing. In some configurations, the host processor can be configured to analyze the sensor signals and to provide a processor output, e.g., formatted as a report that can be printed or displayed on a display. The host processor may analyze two or more of the sensed signals together and/or may use information from one sensed signal to analyze another sensed signal.

In some scenarios, the electronic test plate may include electronic circuitry, e.g., a processor, configured to provide some or all of the control and/or analysis of the sensor signals. In other embodiments, the electronic test plate may transfer sensor signals, e.g., in analog or digital form, to an external processor for the analysis to be performed. The electronic test plate may be configured to include wired or wireless communication circuitry to transfer data, control signals, and/or other information to and/or from the host processor.

Analysis of the sensor signals by the processor may yield an output that includes one or more characteristics of the substance to be analyzed. A non-limiting set of characteristics of the substance includes lateral and vertical impedance, optical spectrum, phenotypic signature, chemical signature, functional signature, acoustic signature, mechanical signature, produced oxygen, cell attachment and spreading, cell proliferation, cellular signal transduction, toxicity, cellular electroporation, cell location, cell count, cell viability, cell stiffness, matrix (gel) stiffness, extracellular pH, motility, and lateral and/or vertical migration of the substance, response to therapeutics, response to environmental challenges, and/or behaviors directed by the cell cytoskeleton to be analyzed.

Analysis of the sensor signals by the processor and data analysis software such as MatLab (as a rapid prototyping language), principal component analysis (as a classical data analysis method), ANOVA for testing significance of differences between groups (e.g., cell populations), and linear regression for predicting a response variable (e.g., impedance) as a function of explanatory variables (time, temperature, etc.) may yield an output that includes one or more characteristics of the substance to be analyzed and may enable capture of new polymodal signatures that are not equal to sum of two or more characteristics of the substance to be analyzed. In some embodiments where the number of test wells or time of continuous monitoring are maximized, high throughput analysis of data may enable identification of new patterns and signatures.

Analysis of the sensor signals may allow stratification of cancer cell colonies by invasiveness, structure, and growth, provide signatures of progression from normal to metastatic cancer disease, or predict substance characteristics from a panel of polysensor measurements. In some embodiments some or all of the test wells are exposed to analytes such as drugs or toxicants (e.g. environmental, chemical, or biological) and cellular responses to the analytes are measured continuously and/or in parallel.

In some embodiments, the analysis of the sensor signals may include determining the optical spectrum of the substance. For example, cells or tissue components may be optically characterized by switching an input light source directed toward the test wells through several wavelengths, such as red, green, and blue, and measuring the optical response. For example, the intensity of light reflected by or transmitted through the substance being analyzed may be measured over the spectrum of input wavelengths using the optical sensors (e.g., PIN photodiodes) associated with the test wells. The input light source and optical sensors of the electronic test plate can additionally or alternatively be used to measure the location, movement and/or morphology of the cells based on absorption, transmission and/or reflection of the input source light by the substance. Image analysis tools such as location and/or edge algorithms can be applied to the outputs of the photodiodes in the photodiode arrays to determine location of the cells within the wells.

By analyzing the signals from the one or more optical sensors associated with a test well, cell movement and/or morphology may be determined based on the amount of input light absorbed and/or reflected by the substance to be analyzed. Additionally or alternatively, cell movement and/or morphology may be determined based on the acoustic signature of the substance. The acoustic response of the substance to be tested changes with cell movement and/or with changes in cell or tissue morphology. The acoustic response may comprise the reflected strength, frequency and/or phase of the acoustic signal and can be used to deduce mechanical properties of the substance to be measured, such as stiffness, mass, and distribution of cells.

Cell movement and/or changes in cell morphology can additionally or alternatively be detected based on impedance sensing. In some implementations, multiple sensors may be employed to detect cell movement. For example, the acoustic, impedance, and/or optical signature of the substance may be compared to one or more known or previously obtained signatures to determine cell movement and/or morphological changes. Additionally or alternatively, microscope imaging may also be employed to measure or confirm cell movement and morphology.

Cell viability may be determined, for example, based on impedance, morphology and/or acoustic signatures of the substance. Upon cell death, changes in the cellular impedance, morphology, and acoustic signatures change. Known signatures of viable cells may be compared to subsequently taken signatures to determine whether or not or to the extent which cells remain viable.

In some embodiments, the chemical sensors of the test plate may additionally or alternatively be used to determine cell viability. Cell death may be indicated when the pH of cells drops from normal to below 7. Additionally or alternatively, cell viability may be determined or confirmed using LIVE/DEAD Viability/Cytotoxicity cell-impermeant stains that only cross compromised or damaged cell membranes along with microscopy.

Mechanical properties and/or morphology of motile cells are distinguishable from the properties and/or morphology of cells and these changes can be detected by analyzing the acoustic response of the substance to be tested. The use of an acoustic sensor enables vertical and lateral measurement of the cell colony position and vertical and lateral migration of the cells. The use of acoustic sensors in parallel enables measurements of cellular mechanical properties, vertical and lateral position of colonies, and vertical and lateral migration of the cells at high throughput.

The processor can be configured to compare signals from neighboring wells that differ in only one respect. Such analysis can provide differential information allowing high levels of common mode noise rejection. For example, acoustic echoes from various interfaces can be accurately subtracted from signals derived from wells whose contents differ only in the presence or absence of cells. Reflections from walls, etc. will in general be common to the two wells and can be subtracted. In a similar manner signals from the same well taken at different times can be subtracted from each other to provide only the time-changing aspects.

Some embodiments involve the use of larger, e.g., 5 mm diameter, test wells to utilize a large number of polysensing pixels. The use of large diameter wells and many pixels provide more signature data to extract cell position, viability and/or other characteristics. Cellular position, viability and/or other characteristics may be calibrated under known initial counts, e.g., 20K, 10K, and 5K wells, and known viability, e.g., >85% per well. Both lateral and vertical motility may be measured over a fixed distance after 24 hours of culture via synthesizing data from optical, acoustic, and electrical impedance measurements. A motility index can be determined from these measurements confirmed or refined through correlation with optical microscopy measurements.

Phenotypic signature is the conglomerate of multiple cellular processes involving gene and protein expression that result in the elaboration of a cell's particular morphology and function. Phenotypic signature can be determined using the sensors of the electronic test plate based on cellular morphology, 3D structure and motility of the cells.

In some embodiments, the one or more electronic test plates, the fluidics subsystem and/or the dispensable materials may be housed within an incubator 640, e.g., a portable incubator, that provides a controlled test environment. In one configuration, parallel real-time sensing and phenotyping can be implemented using the system shown in FIG. 7. The environmental parameters of the incubator 640 may be controlled by the host processor 630 to provide an environment conducive to the test being performed.

Figure 7:
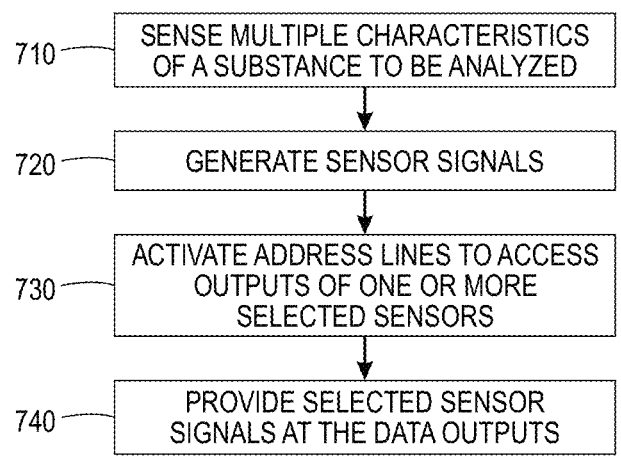
FIG. 7 is a flow diagram illustrating a method of using a bioelectronic test plate and data output processing in accordance with some embodiments.

FIG. 7 is a flow diagram illustrating a method in accordance with some embodiments. Multiple characteristics of a substance to be analyzed are sensed 710 over time using a plurality of sensors arranged so that multiple sensors are associated with each well of a test plate into which the substance is disposed. At least one of the multiple sensors associated with the well is configured to sense a characteristic of the substance that is different from a characteristic sensed by another of the multiple sensors associated with the test well. Electrical sensor signals are generated 720 based on the sensed characteristics. Select lines are activated 730 to access signals of one or more selected sensors so that sensor signals of the selected sensors are provided 740 at the data outputs. According to some embodiments, providing the sensor signals involves providing the sensor signals in simultaneously on a parallel data bus. Using the method outlined in FIG. 7, the substance can be monitored substantially continuously during a test protocol.

In some embodiments, the sensor signals can be conditioned by filtering and/or amplification. When amplifiers are used to condition the sensor signals is can be useful to use a differential amplifier that provides common mode rejection to enhance the signal to noise ratio of the amplified sensor signal. As discussed above, sensing the multiple characteristics of the substance can include sensing at least one characteristic in multiple dimensions.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

What is claimed is:

1. A device comprising:
   a test plate comprising plurality of wells, each well configured to contain a substance to be analyzed; and sensors configured to sense characteristics of the substance and to generate sensor signals based on the sensed characteristics, the sensors arranged so that multiple sensors are associated with each well, at least one sensor of the multiple sensors configured to sense a characteristic of the substance that is different from a characteristic sensed by another sensor of the multiple sensors; and sensor select circuitry coupled to the sensors, the sensor select circuitry arranged on a backplane disposed along the test plate, the sensor select circuitry configured to enable the sensor signals of selected sensors to be accessed at a data output.

2. The device of claim 1, wherein the device includes one or more optically transparent regions that allow each well to be optically interrogated.

3. The device of claim 1, wherein at least one of the sensor select circuitry and the sensors comprise thin film transistors (TFT).

4. The device of claim 1, wherein the multiple sensors comprise two or more of electrical, chemical, optical, acoustic and oxygen sensors.

5. The device of claim 1, wherein the sensor signals include information about one or more of impedance, optical spectrum, phenotypic signature, biophysical signature, chemical signature, functional signature, mechanical signature, cellular locomotion, cell attachment and spreading, cell invasion, cell proliferation, cellular signal transduction, cellular pathways, toxicity, cellular electroporation, cell location, cell count, cell viability, cell stiffness, matrix stiffness, extracellular pH, motility, lateral migration and vertical migration of the substance, and behaviors directed by the substance to be analyzed.

6. The device of claim 1, wherein the substance comprises live cells, bacteria, viruses, fungus, microbes, cell compartments, exosomes, molecules, macromolecules, enzymes or tissue components grown in a three dimensional environment.

7. The device of claim 6, wherein at least one of the multiple sensors in a 2D or 3D well is configured to sense a characteristic of the substance over time.

8. The device of claim 6, wherein at least one of the multiple sensors is a 3D sensor configured to sense a characteristic of the substance along a lateral direction within the well and along a vertical direction within the well.

9. The device of claim 7, wherein the 3D sensor comprises an impedance sensor or an acoustic sensor.

10. The device of claim 1, wherein:
the multiple sensors are arranged in proximity to one another as a sensing pixel;
each of the multiple sensors is a sensing subpixel of the pixel; and
the device includes multiple sensing pixels.

11. The device of claim 10, wherein there are multiple sensing pixels associated with each test well.

12. The device of claim 1, wherein at least one of the test plate and a cap layer disposed over the test wells are sterilizable using at least one of radiation, gas, and heat sterilization.

13. A system, comprising:
a test plate comprising plurality of wells, each well configured to contain a substance to be analyzed;
sensors configured to sense characteristics of the substance and to generate sensor signals based on the sensed characteristics, the sensors arranged so that multiple sensors are associated with each well, at least one sensor of the multiple sensors configured to sense a characteristic of the substance that is different from a characteristic sensed by another sensor of the multiple sensors;

sensor select circuitry coupled to the sensors, the sensor select circuitry arranged on a backplane that extends along the test plate, the sensor select circuitry configured to enable the sensor signals of selected sensors to be accessed at a data output; and readout circuitry configured to receive and process the selected sensor signals present at the data output.

14. The system of claim 13, wherein the readout circuitry comprises at least one of:
signal processing circuitry comprising at least one of an amplifier configured to amplify the selected sensor signals and an analog to digital converter configured to digitize the selected sensor signals; and
communication circuitry configured to transfer the digitized selected sensor signals to a host processor.

15. The system of claim 13, further comprising a fluidics subsystem, comprising at least one of:
a functional film disposed on the test plate and configured to guide the substance loading into the wells via dip coating;
a chemical or physical surface modification of the test plate configured to provide adherence of the substance to each well; and
a component to deliver and/or withdraw material from the wells.

16. The system of claim 13, further comprising a processor configured to analyze the sensor signals and to generate a processor output that provides values for one or more test parameters, wherein the test parameters include one or more of impedance, optical spectrum, phenotypic signature, biophysical signature, chemical signature, functional signature, mechanical signature, cellular locomotion, cell attachment and spreading, cell invasion and extravasation, cell proliferation, cellular signal transduction, cellular pathways, toxicity, cellular electroporation, cell location, cell count, cell viability, cell stiffness, matrix stiffness, extracellular pH, motility, lateral migration and vertical migration of the substance, response to therapeutics, response to environmental challenges, and behaviors directed by the substance to be analyzed.

17. The system of claim 13, further comprising a processor configured to compare signals from neighboring wells that differ in only one respect to provide differential information that allows common mode noise rejection.

18. The system of claim 13, wherein the electronic test plate includes a chemical or physical surface modification configured to increase the sensitivity of a sensor signal when compared to the sensor signal generated without the surface modification.

19. A method of making a device, comprising:
forming a test plate comprising a plurality of wells, each well configured to contain a substance to be analyzed;
fabricating multiple sensors configured to sense characteristics of the substance and to generate sensor signals based on the sensed characteristics; and
fabricating sensor select circuitry coupled to the sensors, the sensor select circuitry configured to enable the sensor signals of selected sensors to be accessed at a data output; and
arranging the sensors with respect to the wells so that multiple sensors are associated with each well, each of the multiple sensors associated with a well configured to sense a characteristic of the substance that is different from characteristics sensed by another sensor of the multiple sensors.

20. The method of claim 19, further comprising capping the wells with a cap layer to protect the substance from at least one of contamination and deterioration.

21. The method of claim 19, further comprising forming functional films via at least one of chemical and physical modification of wells.

22. The method of claim 19, further comprising forming hybrid matrices including at least one of nanomaterials and thermoresponisve 3D gels.

23. The method of claim 19, wherein forming the test plate, fabricating the sensors and sensor select circuitry, and arranging the sensors comprises making the device as a unitary integrated electronic test plate.

24. The method of claim 19, wherein:
forming the test plate comprises forming the test plate as a first subassembly having the wells disposed therein;
fabricating a backplane that includes at least some of the sensors and the sensor select circuitry as a second subassembly separate from the first subassembly; and
arranging the sensors with respect to the wells comprises positioning and bonding the test plate to the backplane.

25. A method, comprising:
sensing over time multiple characteristics of a substance to be analyzed disposed in wells of a test plate using multiple sensors associated with each well, at least one of the multiple sensors configured to sense a characteristic of the substance that is different from a characteristic sensed by another of the multiple sensors;
generating sensor signals based on the sensed characteristics;
activating address lines to enable sensor signals of selected sensors to be accessed at a data output.

26. The method of claim 25, wherein providing the sensor signals comprises providing the sensor signals on a parallel bus.

27. The method of claim 25, wherein generating the sensor signals comprises providing substantially continuous monitoring of the substance.

28. The method of claim 25, wherein sensing the multiple characteristics of the substance comprises sensing at least one characteristic in multiple dimensions over time.

29. A device comprising:
a test plate including:
a plurality of wells, each well configured to contain a substance to be analyzed; and
a plurality of acoustic sensors, each acoustic sensor of the plurality of acoustic sensors respectively coupled to one well of the plurality of well; and
sensor select circuitry coupled to the plurality of acoustic sensors, the sensor select circuitry arranged on a backplane disposed along the test plate, the sensor select circuitry configured to enable sensor signals of selected sensors to be accessed at a data output.

* * * * *